(12) United States Patent
Arakawa et al.

(10) Patent No.: US 12,248,550 B2
(45) Date of Patent: *Mar. 11, 2025

(54) DETECTION OF ATTACHMENT PROBLEM OF APPARATUS BEING WORN BY USER

(71) Applicant: NEC Corporation, Tokyo (JP)

(72) Inventors: Takayuki Arakawa, Tokyo (JP); Takafumi Koshinaka, Tokyo (JP)

(73) Assignee: NEC CORPORATION, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 18/482,245

(22) Filed: Oct. 6, 2023

(65) Prior Publication Data

US 2024/0045938 A1 Feb. 8, 2024

Related U.S. Application Data

(63) Continuation of application No. 18/070,875, filed on Nov. 29, 2022, now Pat. No. 11,977,617, which is a
(Continued)

(30) Foreign Application Priority Data

Aug. 19, 2016 (JP) .................................. 2016-161413

(51) Int. Cl.
*G06F 21/32* (2013.01)
*A61B 5/1171* (2016.01)
(Continued)

(52) U.S. Cl.
CPC ............ *G06F 21/32* (2013.01); *A61B 5/1171* (2016.02); *G06F 21/34* (2013.01); *G10L 17/02* (2013.01);
(Continued)

(58) Field of Classification Search
CPC ............ G06F 21/32; G06F 21/34; H04R 1/10
See application file for complete search history.

(56) References Cited

U.S. PATENT DOCUMENTS

| 5,787,187 A | 7/1998 | Bouchard | ............... A61B 5/12 235/382 |
| 9,648,409 B2 | 5/2017 | Puskarich | ............ H04R 1/1041 |

(Continued)

FOREIGN PATENT DOCUMENTS

| EP | 2037421 A1 | 3/2009 | ......... G07C 9/00158 |
| JP | 2005-032056 A | 2/2005 | |

(Continued)

OTHER PUBLICATIONS

JP Office Action for JP Application No. 2021-146588, mailed on Aug. 2, 2022 with English Translation.
(Continued)

*Primary Examiner* — Shaun Roberts

(57) ABSTRACT

Provided is to prevent a false determination due to an attachment condition of an apparatus that transmits and receives an acoustic signal, and perform accurate personal authentication. A personal authentication device includes: a personal authentication means that authenticates an individual by using first information at least including an acoustic characteristic calculated from an acoustic signal propagating through the head of the user, which is detected by an apparatus being attached on a head of a user for transmitting and receiving the acoustic signal, and a feature amount extracted from the acoustic characteristic; an attachment trouble rule storage means that stores an attachment trouble rule for detecting an attachment trouble with the apparatus; and an attachment trouble detection means that detects a trouble with an attachment state of the apparatus when the first information satisfies the attachment trouble rule.

9 Claims, 21 Drawing Sheets

Related U.S. Application Data continuation of application No. 16/325,849, filed as application No. PCT/JP2017/028531 on Aug. 7, 2017, now Pat. No. 11,537,695.

(51) Int. Cl.

| | | |
|---|---|---|
| *G06F 21/34* | (2013.01) | |
| *G10L 17/02* | (2013.01) | |
| *G10L 19/02* | (2013.01) | |
| *G10L 25/06* | (2013.01) | |
| *G10L 25/51* | (2013.01) | |
| *H04R 1/10* | (2006.01) | |
| *H04R 1/26* | (2006.01) | |
| *H04R 1/46* | (2006.01) | |
| *H04R 3/00* | (2006.01) | |

(52) U.S. Cl.
CPC .............. *G10L 19/02* (2013.01); *G10L 25/06* (2013.01); *G10L 25/51* (2013.01); *H04R 1/10* (2013.01); *H04R 1/1041* (2013.01); *H04R 1/1091* (2013.01); *H04R 1/26* (2013.01); *H04R 1/46* (2013.01); *H04R 3/00* (2013.01)

(56) References Cited

U.S. PATENT DOCUMENTS

| | | | |
|---|---|---|---|
| 2007/0270988 A1 | 11/2007 | Goldstein | H04R 5/04 381/309 |
| 2009/0208027 A1 | 8/2009 | Fukuda | H04R 3/02 381/71.6 |
| 2010/0328033 A1 | 12/2010 | Kamei | G06V 40/12 340/5.82 |
| 2010/0329481 A1 | 12/2010 | Fukuda | H04R 1/1083 381/94.1 |
| 2011/0286615 A1 | 11/2011 | Olodort | H04R 1/1025 381/311 |
| 2012/0116767 A1 | 5/2012 | Hasdell | G10L 25/00 704/254 |
| 2012/0195440 A1 | 8/2012 | Yamagishi | |
| 2013/0216078 A1 | 8/2013 | Bewley | H04R 25/65 381/322 |
| 2013/0236027 A1 | 9/2013 | Tao | H04R 3/00 381/74 |
| 2015/0281826 A1 | 10/2015 | Huang | H04R 1/1008 381/74 |
| 2016/0066822 A1 | 3/2016 | Shennib | A61B 5/123 600/559 |
| 2016/0212522 A1 | 7/2016 | Lee | B60W 50/14 |
| 2017/0078780 A1 | 3/2017 | Qian | H04R 1/1041 |
| 2017/0214994 A1 | 7/2017 | Gadonniex | H04R 1/105 |

FOREIGN PATENT DOCUMENTS

| | | | |
|---|---|---|---|
| JP | 2012080440 A | 4/2012 | |
| JP | 2014-184025 A | 10/2014 | |
| WO | WO-2010133991 A1 | 11/2010 | ........... H04B 13/005 |
| WO | 2014061578 A1 | 4/2014 | |

OTHER PUBLICATIONS

Takayuki Arakawa et al., "Accurate Person Authentication Using Ear Canal Acoustic Features", 2-P-30, Paper at 2016 Spring Meeting of the Acoustical Society of Japan, 2 pages total
International Search Report of PCT/JP2017/028531 dated Oct. 17, 2017 [PCT/ISA/210].
Written Opinion of PCT/JP2017/028531 dated Oct. 17, 2017 [PCT/ISA/237].

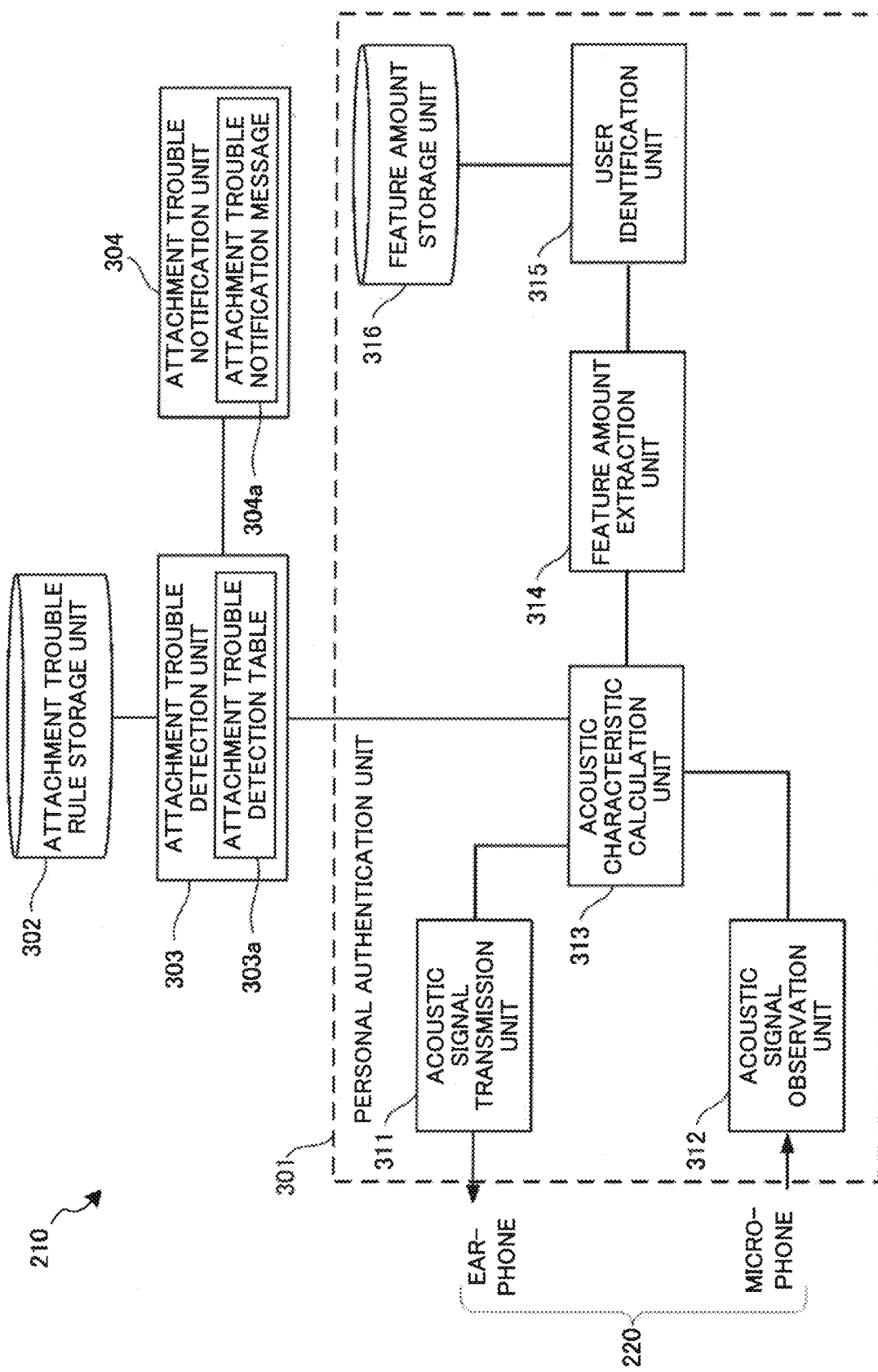

Fig. 5A

| ATTACHMENT TROUBLE RULE NUMBER | SUBJECT FACTOR OF ACOUSTIC CHARACTERISTIC | ATTACHMENT TROUBLE CONDITION | | | COMBINATION ALGORITHM OF ATTACHMENT TROUBLE RULE |
|---|---|---|---|---|---|
| | | FIRST CONDITION | SECOND CONDITION | ... | |
| 11 | VOLUME | $< Th_{11}$ | $> Th_{12}$ | | |
| 12 | VOLUME AT LOW FREQUENCY | $< Th_{21}$ | $> Th_{22}$ | | |
| 13 | VOLUME AT HIGH FREQUENCY | $< Th_{31}$ | $> Th_{32}$ | | |
| 14 | VOLUME OF NATURAL VIBRATION | $< Th_{41}$ | $> Th_{42}$ | | |
| 15 | MAXIMUM VOLUME/PEAK VOLUME | $< Th_{51}$ | $> Th_{52}$ | | |
| 16 | FREQUENCY OF NATURAL VIBRATION | $= \alpha \times Th_{60}$ | $= 1/2 \times Th_{60}$ | | |
| 17 | FREQUENCY OF MAXIMUM VOLUME/PEAK VOLUME | $= \alpha \times Th_{70}$ | $= 1/2 \times Th_{70}$ | | |
| 18 | ONE OR MORE FACTORS | \| SUBJECT FACTOR − AVERAGE OF ACOUSTIC CHARACTERISTIC \| $> T_{80}$ | | | |
| 19 | ONE OR MORE FACTORS | $\approx$ ACOUSTIC CHARACTERISTIC OF TROUBLE | | | |
| 20 | ... | | | | |

| Attachment Trouble Rule Number | Subject Factor of Acoustic Characteristic | Attachment Trouble Condition | | ... | Combination Algorithm of Attachment Trouble Rule |
|---|---|---|---|---|---|
| | | Third Condition | Fourth Condition | | |
| 21 | VOLUME | <(RELATED FACTOR OF AUTHENTICATION SUBJECT)−a1 | >(RELATED FACTOR OF AUTHENTICATION SUBJECT)+a2 | | |
| 22 | FACTOR OF LOW FREQUENCY | <(RELATED FACTOR OF AUTHENTICATION SUBJECT)−b1 | >(RELATED FACTOR OF AUTHENTICATION SUBJECT)+b2 | | |
| 23 | FACTOR OF HIGH FREQUENCY | <(RELATED FACTOR OF AUTHENTICATION SUBJECT)−c1 | >(RELATED FACTOR OF AUTHENTICATION SUBJECT)+c2 | | |
| 24 | VOLUME OF NATURAL VIBRATION | <(RELATED FACTOR OF AUTHENTICATION SUBJECT)−d1 | >(RELATED FACTOR OF AUTHENTICATION SUBJECT)+d2 | | |
| 25 | MAXIMUM VOLUME/PEAK VOLUME | <(RELATED FACTOR OF AUTHENTICATION SUBJECT)−e1 | >(RELATED FACTOR OF AUTHENTICATION SUBJECT)+e2 | | |
| 26 | FREQUENCY OF NATURAL VIBRATION | =β ×(RELATED FACTOR OF AUTHENTICATION SUBJECT) | =1/2 ×(RELATED FACTOR OF AUTHENTICATION SUBJECT) | | |
| 27 | FREQUENCY OF MAXIMUM VOLUME/PEAK VOLUME | =β ×(RELATED FACTOR OF AUTHENTICATION SUBJECT) | =1/2 ×(RELATED FACTOR OF AUTHENTICATION SUBJECT) | | |
| 28 | ... | | | | |

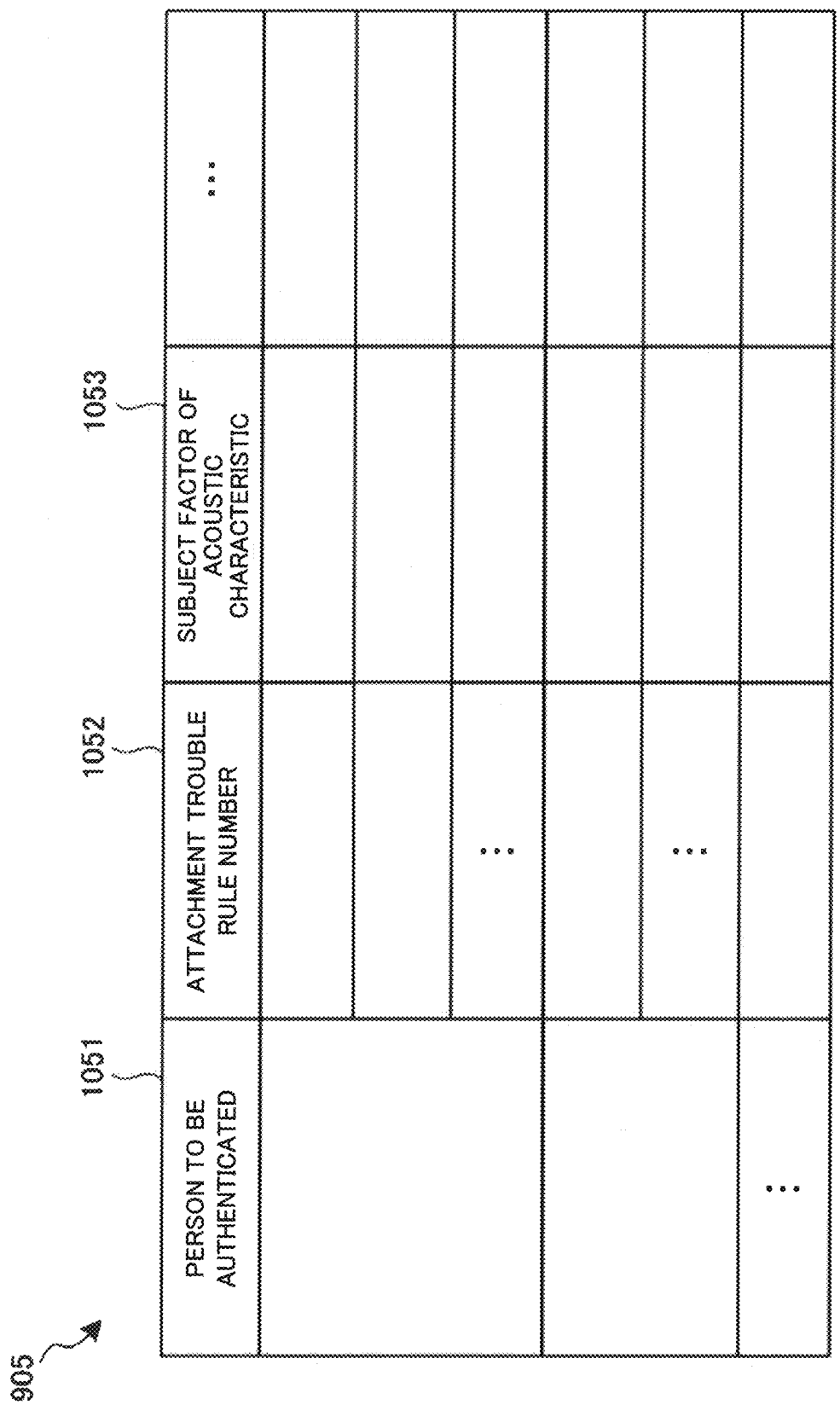

| SUBJECT FACTOR OF ATTACHMENT TROUBLE DETECTION | SUBJECT FACTOR OF ACOUSTIC CHARACTERISTIC (FROM STORAGE UNIT 905) | SUBJECT FACTOR OF ACOUSTIC CHARACTERISTIC (FROM CALCULATION UNIT 313) | ATTACHMENT TROUBLE RULE NUMBER | ATTACHMENT TROUBLE DETERMINATION FLAG | ATTACHMENT TROUBLE DETECTION OUTPUT |
|---|---|---|---|---|---|
| 521 | 1022 | 522 | 1023 | 524 | 525 |
|  |  |  |  |  |  |
|  |  |  |  |  |  |
| ... |  |  |  |  |  |

Fig. 14A

| ATTACHMENT TROUBLE RULE NUMBER | SUBJECT FACTOR OF FEATURE AMOUNT | | ATTACHMENT TROUBLE CONDITION | | | COMBINATION ALGORITHM OF ATTACHMENT TROUBLE RULE |
|---|---|---|---|---|---|---|
| | FEATURE AMOUNT | FACTOR | FIFTH CONDITION | SIXTH CONDITION | ... | |
| 31 | LOGARITHM SPECTRUM | | | | | |
| 32 | | | | | | |
| 33 | | ... | | | | |
| 34 | MEL-CEPSTRUM COEFFICIENT | | | | | |
| 35 | | ... | | | | |
| 36 | LINEAR PREDICTIVE CODING COEFFICIENT | ... | | | | |
| 37 | | | | | | |
| 38 | PRINCIPAL COMPONENT ANALYSIS | | | | | |
| 39 | LINEAR DISCRIMINATIVE ANALYSIS | | | | | |
| 40 | | | | | | |

| SUBJECT FACTOR OF ATTACHMENT TROUBLE DETECTION | SUBJECT FACTOR OF FEATURE AMOUNT | ATTACHMENT TROUBLE RULE NUMBER | ATTACHMENT TROUBLE DETERMINATION FLAG | ATTACHMENT TROUBLE DETECTION OUTPUT |
|---|---|---|---|---|
| 1421 | 1422 | 1423 | 524 | 525 |
|  |  |  |  |  |
|  |  |  |  |  |
| ... |  |  |  |  |

DETECTION OF ATTACHMENT PROBLEM OF APPARATUS BEING WORN BY USER

CROSS-REFERENCE TO RELATED APPLICATIONS

The present application is a continuation application of U.S. patent application Ser. No. 18/070,875 filed on Nov. 29, 2022, which is a continuation application of U.S. patent application Ser. No. 16/325,849 filed on Feb. 15, 2019, which issued as U.S. Pat. No. 11,537,695, which is a National Stage Entry of international application No. PCT/JP2017/028531 filed on Aug. 7, 2017, which claims the benefit of priority from Japanese Patent Application No. 2016-161413 filed on Aug. 19, 2016, the disclosures of all of which are incorporated in their entirety by reference herein.

TECHNICAL FIELD

The present invention relates to a personal authentication system, a personal authentication device, a personal authentication method, a personal authentication program.

BACKGROUND ART

NPL 1 in the technical field discloses a technique for measuring an acoustic characteristic of an ear canal of a user by using an earphone with a built-in microphone, and performing personal authentication by using a difference between individuals in the measured acoustic characteristic of the ear canal.

CITATION LIST

Non Patent Literature

[NPL 1] Takayuki ARAKAWA et al., "Accurate Person Authentication Using Ear Canal Acoustic Features", 2-P-30, Paper at 2016 Spring Meeting of the Acoustical Society of Japan

SUMMARY OF INVENTION

Technical Problem

The techniques described in the above documents do not mention possibility of misjudgment and solution thereof, caused by a malfunction in the installation of equipment that transmits and receives sound signals such as headphones and earphones.

An object of the present invention is to provide a technique for solving the above-described problem.

Solution to Problem

To achieve the above object, a personal authentication device according to the present invention includes:
  a personal authentication means that authenticates an individual by using first information including at least one of
    an acoustic characteristic calculated from an acoustic signal propagating through the head of the user, which is detected by an apparatus being attached on a head of a user for transmitting and receiving the acoustic signal, and
    a feature amount extracted from the acoustic characteristic;
  an attachment trouble rule storage means that stores an attachment trouble rule for detecting an attachment trouble with the apparatus; and
  an attachment trouble detection means that detects a trouble with an attachment state of the apparatus when the first information satisfies the attachment trouble rule.

To achieve the above object, a personal authentication method according to the present invention includes:
  authenticating an individual by using first information including at least one of
    an acoustic characteristic calculated from an acoustic signal propagating through the head of the user, which is detected by an apparatus being attached on a head of a user for transmitting and receiving the acoustic signal, and
    a feature amount extracted from the acoustic characteristic; and
  detecting a trouble with an attachment state of the apparatus when the first information satisfies an attachment trouble rule for detecting an attachment trouble with the apparatus.

To achieve the above object, a personal authentication program according to the present invention causes a computer to execute:
  processing of authenticating an individual by using first information including at least one of
    an acoustic characteristic calculated from an acoustic signal propagating through the head of the user, which is detected by an apparatus being attached on a head of a user for transmitting and receiving the acoustic signal, and
    a feature amount extracted from the acoustic characteristic; and
  processing of detecting a trouble with an attachment state of the apparatus when the first information satisfies an attachment trouble rule for detecting an attachment trouble with the apparatus.

To achieve the above object, a personal authentication system according to the present invention includes:
  an apparatus that transmits and receives an acoustic signal at a head of a user;
  a personal authentication means that authenticates an individual by using first information which is including at least one of
    an acoustic characteristic calculated from an acoustic signal that is detected by the apparatus being attached and that propagates through the head of the user, and
    a feature amount extracted from the acoustic characteristic;
  an attachment trouble rule storage means that stores an attachment trouble rule for detecting an attachment trouble with the apparatus; and
  an attachment trouble detection means that detects a trouble with an attachment state of the apparatus when the first information satisfies the attachment trouble rule.

Advantageous Effects of Invention

According to the present invention, it is possible to prevent erroneous determination due to the wearing state of a device for transmitting/receiving an acoustic signal, and to perform accurate personal authentication.

BRIEF DESCRIPTION OF DRAWINGS

FIG. 3 is a block diagram illustrating a functional configuration of the personal authentication device according to the second example embodiment of the present invention.

FIG. 5A is a diagram illustrating a configuration of an attachment trouble rule storage unit according to the second example embodiment of the present invention.

FIG. 10A is a diagram illustrating a configuration of an attachment trouble rule storage unit according to the third example embodiment of the present invention.

FIG. 10B is a diagram illustrating a configuration of an acoustic characteristic storage unit according to the third example embodiment of the present invention.

FIG. 10C is a diagram illustrating a configuration of an attachment trouble detection table according to the third example embodiment of the present invention.

FIG. 14A is a diagram illustrating a configuration of an attachment trouble rule storage unit according to the fourth example embodiment of the present invention.

FIG. 14B is a diagram illustrating a configuration of an attachment trouble detection table according to the fourth example embodiment of the present invention.

EXAMPLE EMBODIMENT

Hereinafter, example embodiments of the present invention are illustratively described in detail with reference to drawings. However, a structural component described in the example embodiments below is merely an exemplification, and a technical scope of the present invention is not intended to be limited to the structural component.

First Example Embodiment

Figure 1:
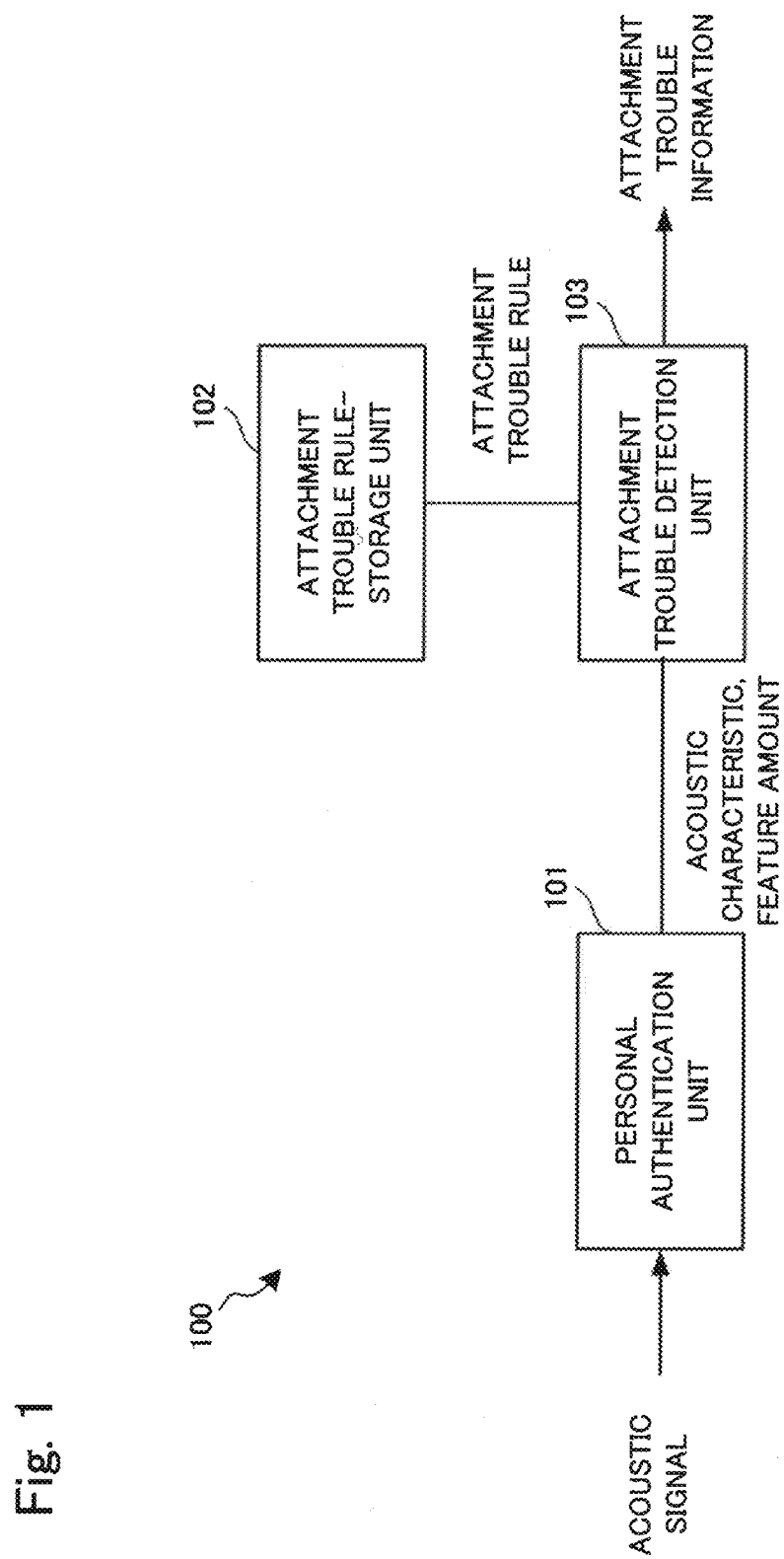
FIG. 1 is a block diagram illustrating a configuration of a personal authentication device according to a first example embodiment of the present invention.

Personal authentication device 100 as a first example embodiment of the present invention is described by using FIG. 1. Personal authentication device 100 is a device for authenticating an individual.

As illustrated in FIG. 1, personal authentication device 100 includes personal authentication unit 101, attachment trouble rule storage unit 102, and attachment trouble detection unit 103. Personal authentication unit 101 authenticates an individual by using, as first information, at least any of an acoustic characteristic calculated from an acoustic signal propagating through a head of a user wearing an apparatus that transmits and receives the acoustic signal and a feature amount extracted from the acoustic characteristic. Attachment trouble rule storage unit 102 stores an attachment trouble rule for detecting an attachment trouble with the apparatus. Attachment trouble detection unit 103 detects a trouble with an attachment state of the apparatus when the first information satisfies the attachment trouble rule.

According to the present example embodiment, when an acoustic characteristic acquired from an acoustic signal propagating through a head of a user and a feature amount satisfy an attachment trouble rule for detecting an attachment trouble with an apparatus, a trouble is detected in an attachment state of the apparatus. In this way, a false determination due to an attachment condition of the apparatus that transmits and receives an acoustic signal can be prevented, and accurate personal authentication can be performed.

Second Example Embodiment

Next, a personal authentication device according to a second example embodiment of the present invention is described. The personal authentication device according to the present example embodiment stores an attachment trouble rule for detecting an attachment trouble with a wearable apparatus, and detects a trouble with an attachment state of the apparatus when an acoustic characteristic acquired from an acoustic signal by a personal authentication unit satisfies the attachment trouble rule for detecting an attachment trouble with the apparatus. In the present example embodiment, the attachment trouble rule is a rule that determines an attachment trouble, based on a comparison between an acoustic characteristic and a predetermined reference. Then, the trouble with the attachment state of the apparatus is notified.

(Acoustic Characteristic)

Note that, for example, an impulse response, a transfer function acquired by performing a Fourier transform or a Laplace transform on an impulse response are conceivable as an acoustic characteristic. The acoustic characteristic includes, for example, information about how an acoustic signal is reflected and/or declines in a living body. When an earphone and a microphone are attached at an ear canal opening, and an acoustic characteristic reflected in the ear canal is measured, an ear canal impulse response and an ear canal transfer function may be used as an acoustic characteristic.

<<Overview of Personal Authentication System>>

Figure 2:
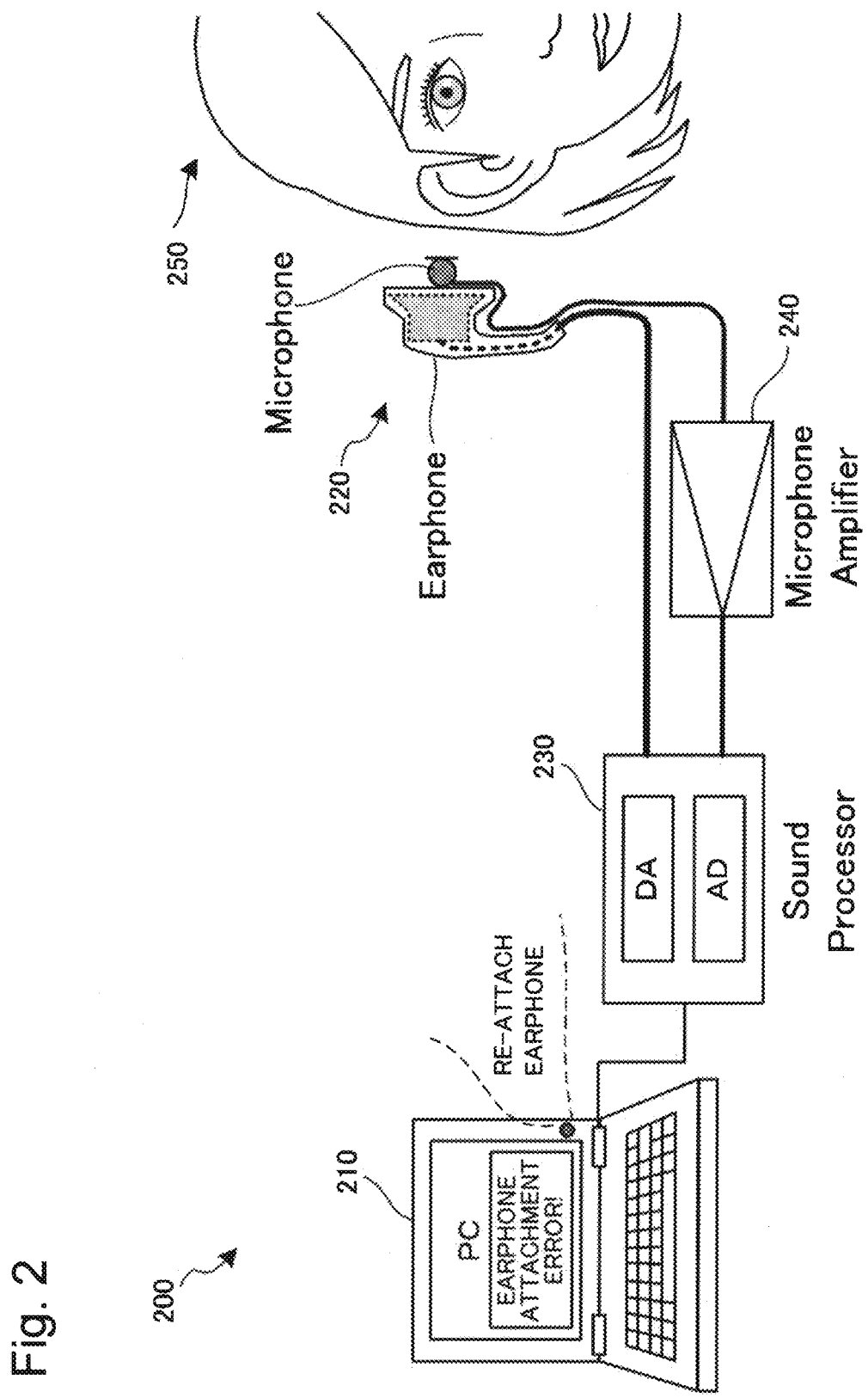
FIG. 2 is a diagram illustrating an overview of a personal authentication system including a personal authentication device according to a second example embodiment of the present invention.

FIG. 2 is a diagram illustrating an overview of personal authentication system 200 including personal authentication device 210 according to the present example embodiment.

Personal authentication system 200 illustrated in FIG. 2 includes personal authentication device 210 as a personal computer (PC), attached apparatus 220 including an earphone and a microphone, sound processor 230, and microphone amplifier 240. Note that, reference sign 250 indicates a user (subject) to be recognized.

Note that, it is desirable that a microphone and an earphone are integrally formed in such a way as not to change a relative positional relationship thereof. However, this is non-essential when a relative positional relationship between a microphone and an earphone does not greatly change. Further, a microphone-integrated earphone that is inserted into an ear canal entrance is taken as attached apparatus 220 herein, but a microphone set in a headphone being a type of covering an auricle may be taken as an example of achieving both a microphone and an earphone. Further, a microphone set in a portion of a telephone receiver may be taken as another example of achieving both a microphone and an earphone. In addition, observing an acoustic signal transmitted from an earphone attached at a left ear canal entrance by a microphone attached at an ear canal entrance of a right ear and vice versa, are also conceivable.

In FIG. 2, personal authentication device 210 has detected an attachment trouble with attached apparatus 220, and thus voice of "re-attach earphone" is output from a speaker, or "earphone attachment error!" is displayed on a screen. Note that, an attachment trouble may be notified by an alarm from attached apparatus 220 instead of personal authentication device 210.

<<Functional Configuration of Personal Authentication Device>>

FIG. 3 is a block diagram illustrating a functional configuration of personal authentication device 210 according to the present example embodiment.

With reference to FIG. 3, personal authentication device 210 in the present example embodiment includes personal authentication unit 301 that verifies an individual from an acoustic characteristic of an acoustic signal propagating through a head of a user. Then, personal authentication device 210 includes attachment trouble rule storage unit 302 that stores an attachment trouble rule, attachment trouble detection unit 303 that detects a trouble with an attachment state of attached apparatus 220 when the acoustic characteristic satisfies the attachment trouble rule, and attachment trouble notification unit 304 that notifies the trouble with the attachment state.

Attachment trouble detection unit 303 includes attachment trouble detection table 303a, compares an acoustic characteristic calculated in acoustic characteristic calculation unit 313 of personal authentication unit 301 with a condition of an acoustic characteristic stored in attachment trouble rule storage unit 302, and detects a trouble with an attachment state. Attachment trouble notification unit 304 includes attachment trouble notification message 304a, and outputs a message related to an attachment trouble.

Personal authentication unit 301 includes acoustic signal transmission unit 311, acoustic signal observation unit 312, acoustic characteristic calculation unit 313, feature amount extraction unit 314, user identification unit 315, and feature amount storage unit 316.

Acoustic signal transmission unit 311 transmits an acoustic signal to a part of a head of a user via an earphone. Herein, the part of the head to which the acoustic signal is transmitted is more specifically a region of the head in which a cavity is formed, and may be at least a part of a region to which an accessory and an apparatus generating an acoustic effect can be attached or brought close.

Acoustic signal observation unit 312 observes an acoustic signal that has been transmitted from acoustic signal transmission unit 311 and propagated through a part of a head of a user. The part of the head as a propagation path of the acoustic signal may be more specifically at least a part of a skull, a brain, a sensory organ, and a cavity therebetween, constituting the head.

Acoustic characteristic calculation unit 313 calculates an acoustic characteristic of an acoustic signal propagating through a part of a head of a user, based on an acoustic signal transmitted from acoustic signal transmission unit 311 and an acoustic signal observed by acoustic signal observation unit 312. Herein, the acoustic characteristic is, such as, an impulse response, a transfer function acquired by performing a fast Fourier transform on an impulse response.

Feature amount extraction unit 314 calculates a feature amount concerned with a user from a calculated acoustic characteristic. As a feature amount, for example, a logarithm spectrum, mel-frequency cepstrum coefficients, linear predictive coding coefficients may be used.

Further, a feature amount acquired by dimensionally compressing a logarithm spectrum, mel-frequency cepstrum coefficients, and linear predictive coding coefficients by using a principal component analysis or a linear discriminative analysis may be used. Further, a feature amount other than this may be used.

User identification unit 315 compares a feature amount acquired by feature amount extraction unit 314 with a feature amount of a registered user stored in feature amount storage unit 316 described later, and determines whether or not a user corresponds to a registered individual.

Feature amount storage unit 316 stores a feature amount previously extracted from a predetermined user. For example, feature amount storage unit 316 stores a feature amount previously extracted from a plurality of users by using acoustic signal transmission unit 311, acoustic signal observation unit 312, acoustic characteristic calculation unit 313, and feature amount extraction unit 314, or a configuration identical to these. A verification method in the authentication is to determine whether or not a person is the same person as a person among people to be verified having a previously stored feature amount, determine a person from a plurality of people to be verified having a previously stored feature amount, or perform these two determinations at the same time.

(Example of Acoustic Characteristic)

Figure 4A:
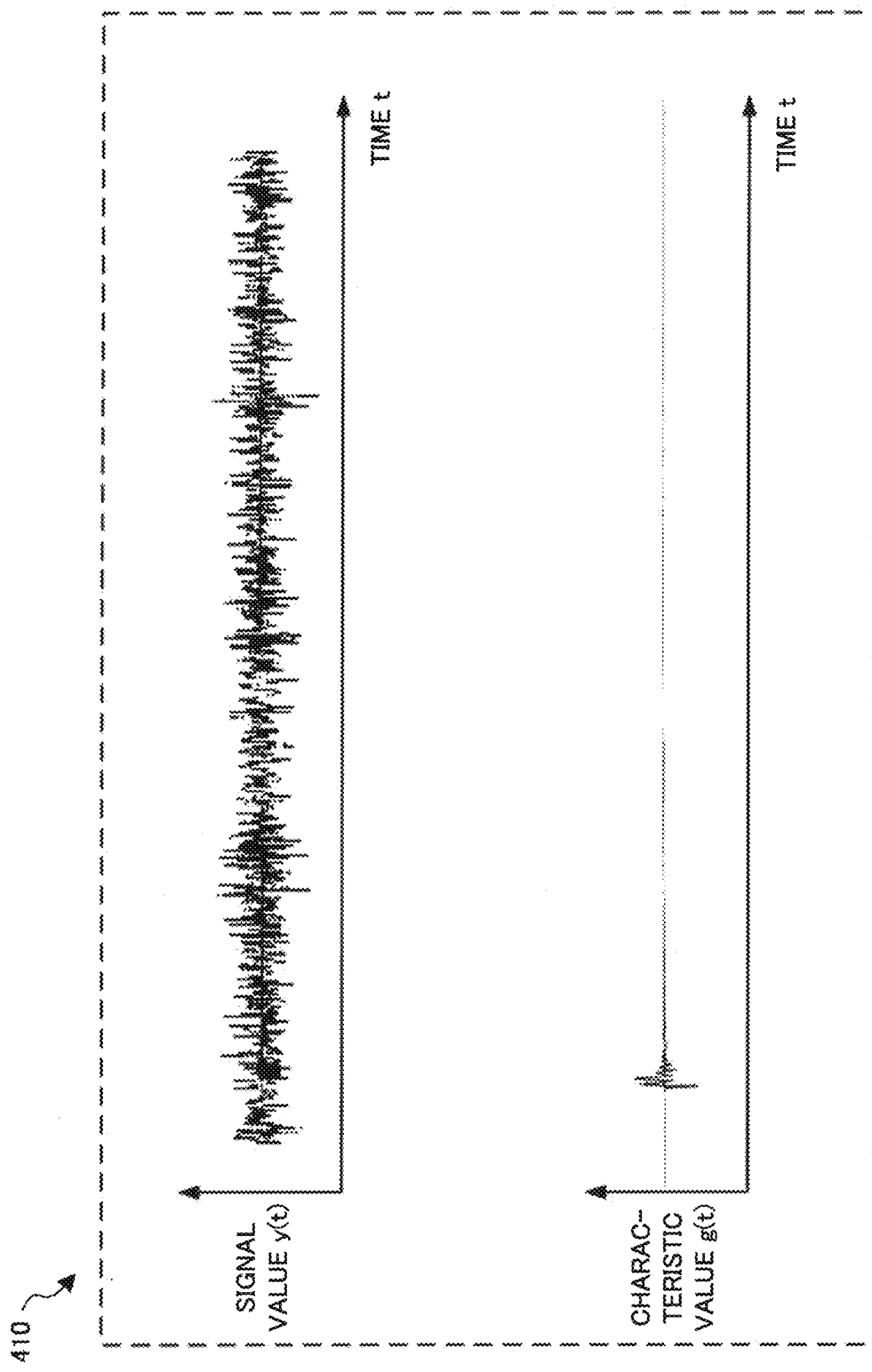
FIG. 4A is a diagram illustrating an acoustic characteristic used for personal authentication according to the second example embodiment of the present invention.
Figure 4B:
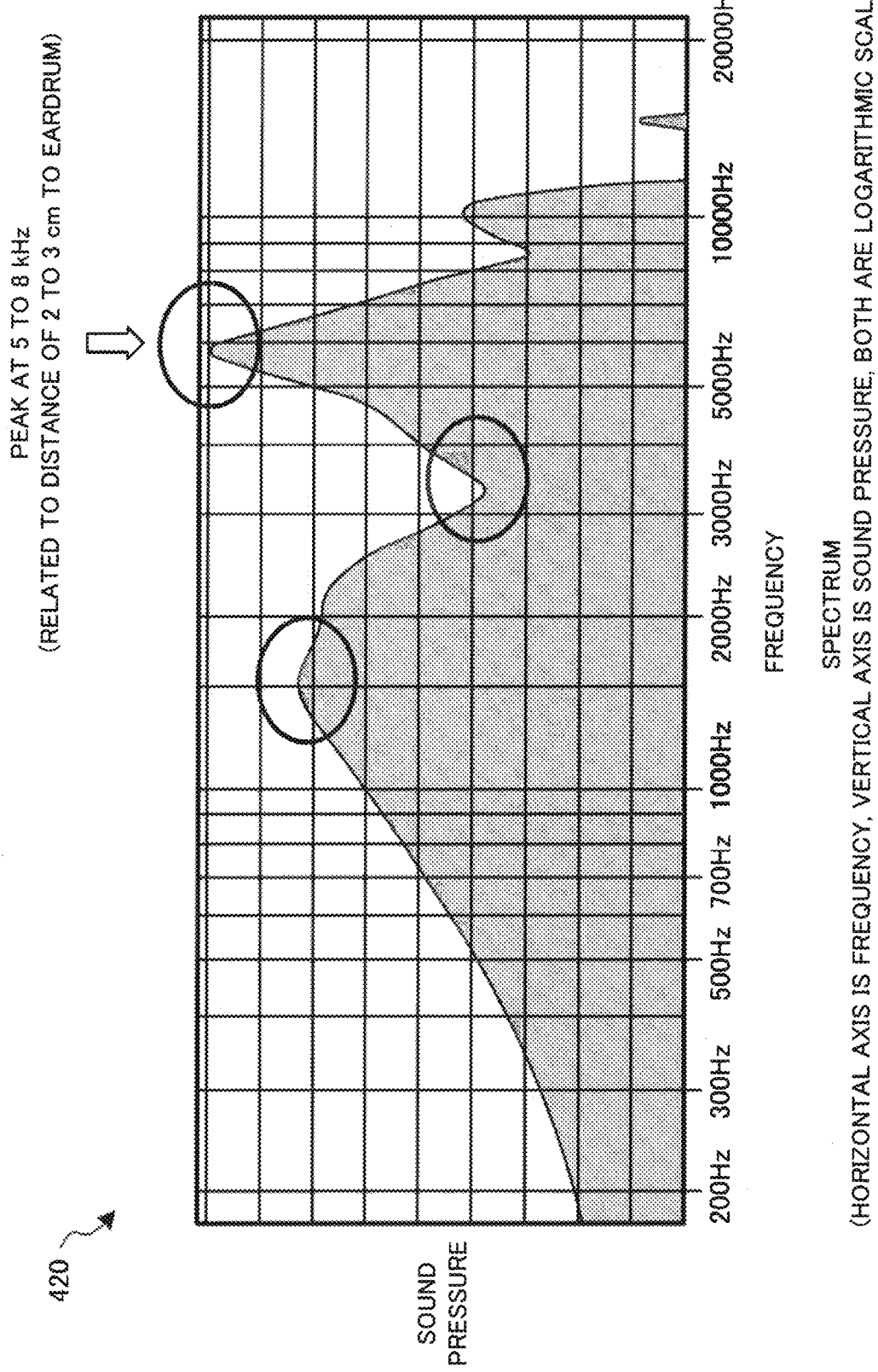
FIG. 4B is a diagram illustrating an acoustic characteristic used for personal authentication according to the second example embodiment of the present invention.

FIGS. 4A and 4B are diagrams illustrating an acoustic characteristic used for personal authentication according to the present example embodiment.

FIG. 4A is a diagram illustrating impulse response 410 as an acoustic characteristic. The impulse response is used for detecting an attachment trouble in the present example embodiment.

Further, FIG. 4B is a diagram of logarithm spectrum 420. When an acoustic characteristic of an ear canal is used in the present example embodiment, as illustrated in FIG. 4B, a peak is observed for a factor concerned with volume of a frequency related to a distance (normally 2 to 3 cm) between acoustic signal transmission unit 311 and an eardrum. For example, a value at this peak may be compared with a predetermined reference value in attachment trouble detection in the present example embodiment. Further, volume indicates power of a spectrum acquired by using an amplitude of a speech waveform, a fast Fourier transform (FFT).
(Detection of Attachment Trouble)

For example, when an attachment state is insufficient and a gap is present, sound leaks to the outside, and thus volume of a volume characteristic becomes lower than that when an attachment state is sufficient. By using this change, an insufficient attachment state can be detected. Further, a change in the volume depends on a shape of an earphone and an attachment state, and characteristically appears at a specific frequency. Thus, detection focusing on volume at a specific frequency is effective.

Furthermore, with reference to FIG. 4B, a peak related to a distance of 2 to 3 cm to an eardrum occurs at 5 to 8 kHz. This can be understood as air column resonance of a tube of 2 to 3 cm with closed ends.
Assuming that the speed of sound is 340 meters per second, a wavelength and natural vibration of the tube with closed ends can be expressed by the following expressions.

$$\lambda n = (2/n) \times L \quad n=1,2,3,\ldots$$

$$fn = (340/2L) \times n \quad n=1,2,3,\ldots$$

Herein, $\lambda n$ represents a wavelength (unit is meter), and fn represents a frequency (unit is Hz). n=1 represents 1 harmonic of natural vibration, and n=2, 3, 4 respectively represent 2 harmonics, 3 harmonics, and 4 harmonics of natural vibration. L represents a length (unit is meter) of an air column, and herein represents a distance from a headphone or an earphone to an eardrum.

In this way, it is considered that a frequency of 1 harmonic of natural vibration could not be observed when a frequency of natural vibration became a constant multiple of equal to or greater than two times a predetermined value, and it can thus be determined that attachment of a headphone or an earphone is insufficient.

A wavelength and natural vibration of a tube of 2 to 3 cm with one open end are expressed by the following expressions.

$$\lambda n = \{4/(2n-1)\} \times L \quad n=1,2,3,\ldots$$

$$fn = \{340/4L\} \times (2n-1) \quad n=1,2,3,\ldots$$

In this way, it is considered that, when a frequency of natural vibration halved, natural vibration of a tube with closed ends changed to that of a tube with one open end, and it can thus be determined that attachment of a headphone or an earphone is insufficient.
(Attachment Trouble Rule-Storage Unit)

FIG. 5A is a diagram illustrating a configuration of attachment trouble rule storage unit 302 according to the present example embodiment. Attachment trouble rule storage unit 302 stores an attachment trouble rule for detecting an attachment trouble from an acoustic characteristic. Note that, a configuration of attachment trouble rule storage unit 302 is not limited to FIG. 5A.

Attachment trouble rule storage unit 302 stores, in association with rule number 511 that identifies an attachment trouble rule, subject factor 512 of acoustic characteristic used for attachment trouble detection, attachment trouble condition 513 in subject factor 512 of acoustic characteristic, and combination algorithm 514 of attachment trouble rules used for attachment trouble detection. Note that, each attachment trouble rule may be used alone.

The following examples of attachment trouble rules in the present example embodiment are conceivable. Herein, a factor represents one or more values among a plurality of values constituting acoustic characteristics.

(Rule Number 11): A value of a factor equivalent to volume among acoustic characteristics is smaller or greater than a predetermined reference.

(Rule Number 12): A value of a factor equivalent to volume at a low frequency (for example, equal to or less than 1 kHz) among acoustic characteristics is smaller than (falls below) or greater than (exceeds) a predetermined reference.

(Rule Number 13): A value of a factor equivalent to volume at a high frequency (for example, equal to or greater than 1 kHz) among acoustic characteristics is smaller or greater than a predetermined reference.

(Rule Number 14): A value of a factor concerned with volume of characteristic vibration/natural vibration related to a distance from an earphone (acoustic transmission unit) to an eardrum among acoustic characteristics is smaller or greater than a predetermined reference.

(Rule Number 15): A maximum value and a value (peak) greater than two adjacent values among factors equivalent to volume of an acoustic characteristic are smaller or greater than a predetermined reference.

(Rule Number 16): A frequency of natural vibration related to a distance from an earphone (acoustic transmission unit) to an eardrum among acoustic characteristics is a constant multiple or half of a predetermined reference.

(Rule Number 17): A frequency of a factor having a maximum value and a factor having a value (peak) greater than two adjacent values, among factors equivalent to volume of an acoustic characteristic, is a constant multiple or half of a frequency of a corresponding factor of an acoustic characteristic acquired from a predetermined person to be authenticated.

(Rule Number 18): One or more factors of an acoustic characteristic are greatly different from an average of acoustic characteristics previously acquired from a plurality of people.

(Rule Number 19): One or more factors of an acoustic characteristic are similar to an acoustic characteristic in which a trouble with attachment is previously found.
(Attachment Trouble Detection Table)

Figure 5B:
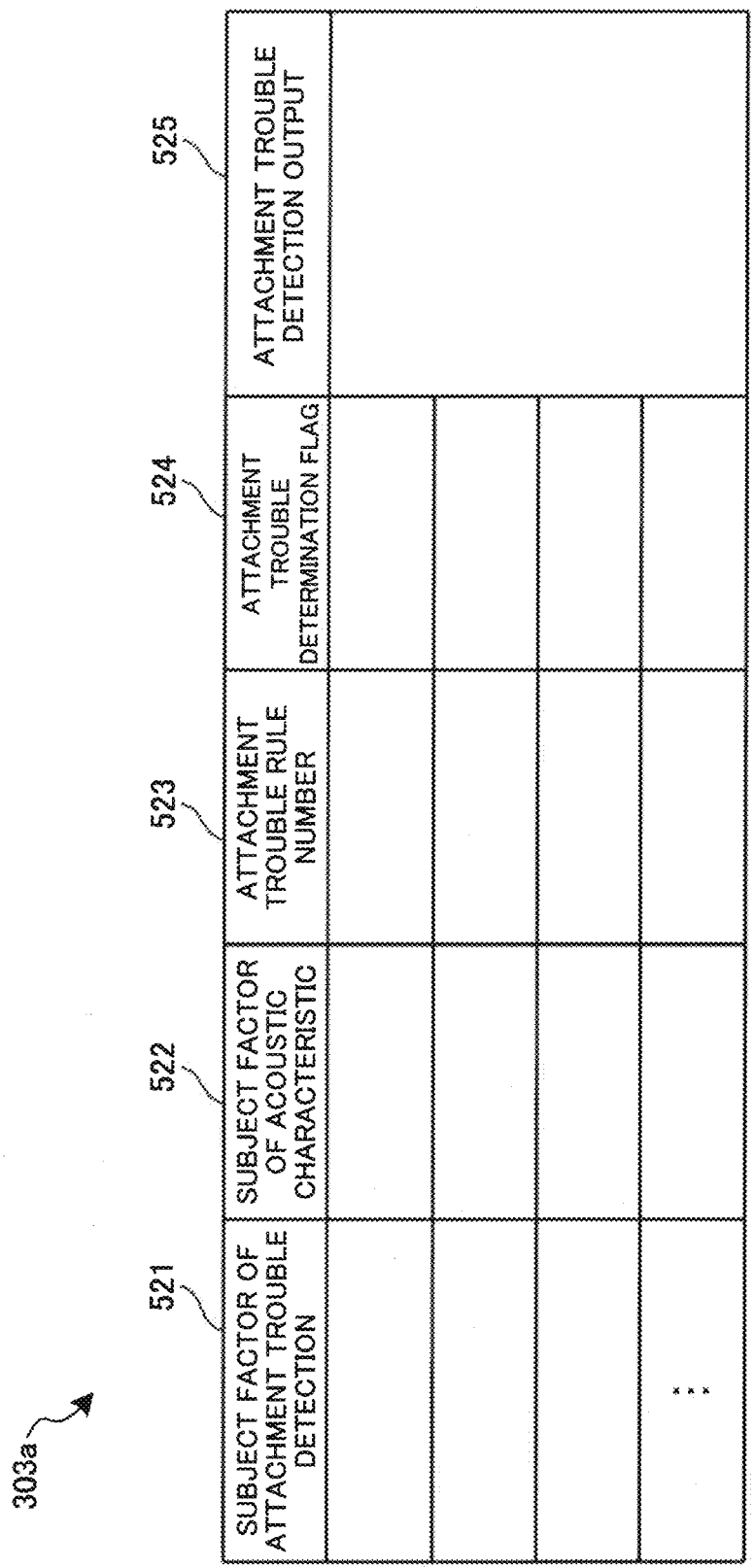
FIG. 5B is a diagram illustrating a configuration of an attachment trouble detection table according to the second example embodiment of the present invention.

FIG. 5B is a diagram illustrating a configuration of attachment trouble detection table 303a according to the present example embodiment.

Attachment trouble detection table 303a is used as a temporary memory for detecting an attachment trouble by attachment trouble detection unit 303.

Attachment trouble detection table 303a stores, in association with subject factor 521 of attachment trouble detection, subject factor 522 of acoustic characteristic from acoustic characteristic calculation unit 313, attachment trouble rule number 523 used for attachment trouble detection, and attachment trouble determination flag 524 when subject factor 522 of acoustic characteristic satisfies a condition of attachment trouble rule number 523. Then, attachment trouble detection table 303a stores attachment trouble detection output 525 that combines attachment trouble determination flag 524 according to combination algorithm 514 of attachment trouble rule.

<<Hardware Configuration of Personal Authentication Device>>

Figure 6:
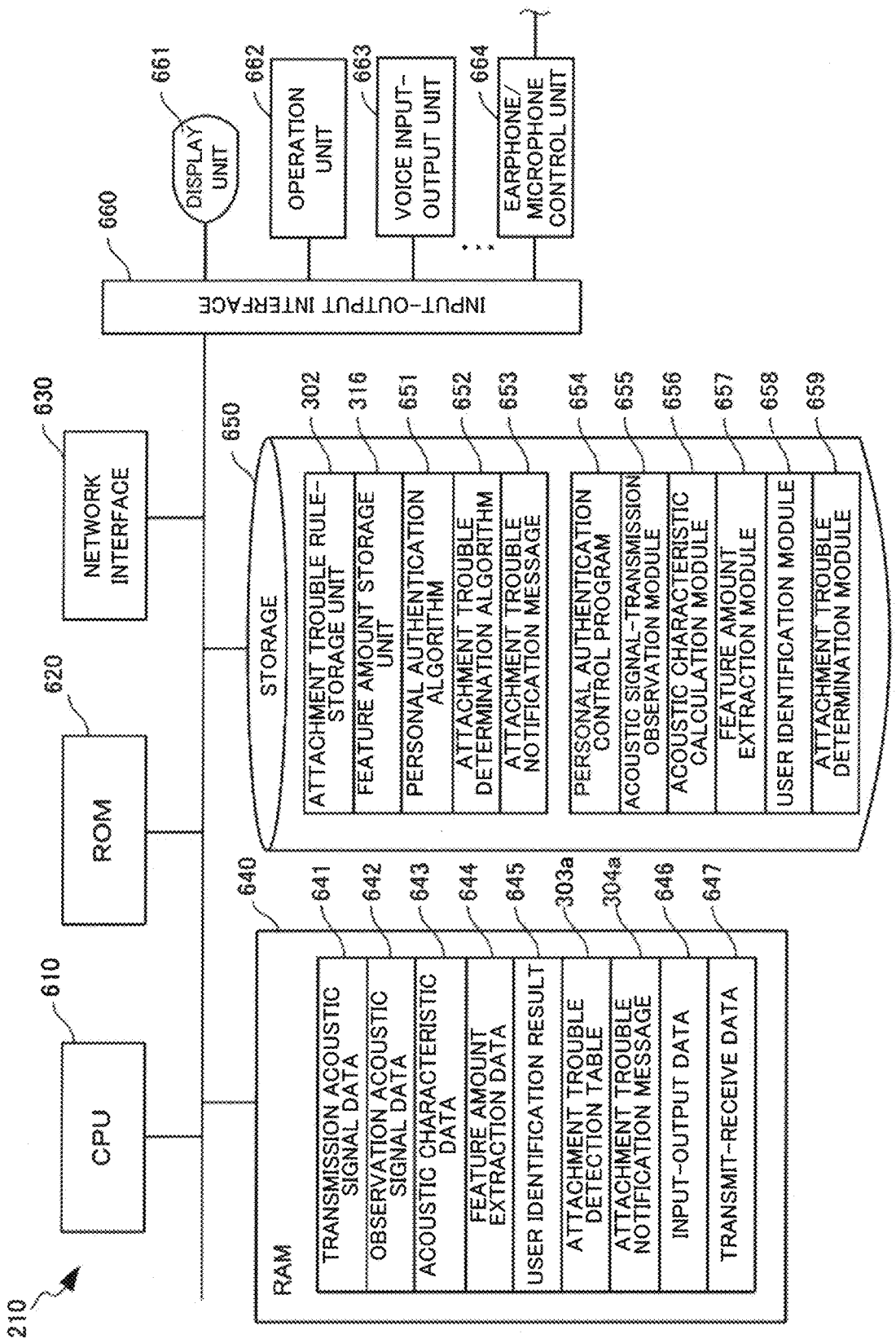
FIG. 6 is a block diagram illustrating a hardware configuration of the personal authentication device according to the second example embodiment of the present invention.

FIG. 6 is a block diagram illustrating a hardware configuration of personal authentication device 210 according to the present example embodiment.

In FIG. 6, CPU 610 is a processor for arithmetic control and achieves the functional structural unit in FIG. 3 by executing a program. ROM 620 stores fixed data, such as initial data and a program, and a program. Network interface 630 controls communication with an external device via a network.

RAM 640 is a random access memory used as a work area for a temporary memory by CPU 610. RAM 640 secures a region in which data needed for achieving the present example embodiment are stored. Transmission acoustic signal data 641 are data about a transmission acoustic signal to an earphone. Observation acoustic signal data 642 are data about an observation acoustic signal from a microphone. Acoustic characteristic data 643 are data about an acoustic characteristic calculated from transmission acoustic signal data 641 and observation acoustic signal data 642 by acoustic characteristic calculation unit 313. Feature amount extraction data 644 are data extracted from acoustic characteristic data 643 by feature amount extraction unit 314. User identification result 645 is data about a user identified from feature amount extraction data 644 and feature amount storage unit 316 by user identification unit 315. Attachment trouble detection table 303a is a table used for detecting an attachment trouble by attachment trouble detection unit 303, which is described with FIG. 5B. Attachment trouble notification message 304a is a message with which attachment trouble notification unit 304 notifies an attachment trouble. Input-output data 646 are data input to and output from a peripheral apparatus via input-output interface 660. Transmit-receive data 647 are data communicated via network interface 630.

Storage 650 stores a database, various parameters, or the following data or program needed for achieving the present example embodiment. Attachment trouble rule storage unit 302 is a database of an attachment trouble rule, which is described with FIG. 5A. Feature amount storage unit 316 is a database that stores a feature amount previously extracted from a predetermined user. Personal authentication algorithm 651 is an algorithm for a personal authentication method in the present example embodiment. Attachment trouble determination algorithm 652 is an algorithm for a method of determining an attachment trouble in the present example embodiment. Attachment trouble notification message 653 is a database that stores a notification message related to an attachment trouble.

The following program is stored in storage 650. Personal authentication control program 654 is a program for controlling personal authentication device 210. Acoustic signal-transmission observation module 655 is a module that controls transmission and observation of acoustic signals. Acoustic characteristic calculation module 656 is a module that calculates an acoustic characteristic from transmitted and observed acoustic signals. Feature amount extraction module 657 is a module that extracts a feature amount from an acoustic characteristic. User identification module 658 is a module that identifies a user from a feature amount extracted from an acoustic characteristic and a feature amount of feature amount storage unit 316. Attachment trouble determination module 659 is a module that determines an attachment trouble with attached apparatus 220 from an acoustic characteristic (or a feature amount) according to an attachment trouble rule.

Input-output interface 660 interfaces input and output with a peripheral apparatus. Display unit 661, operation unit 662, voice input-output unit 663, and earphone/microphone control unit 664 that connects attached apparatus 220 are connected to input-output interface 660.

Note that, a program and data related to a general-purpose function and other achievable function of personal authentication device 210 are not illustrated in RAM 640 and storage 650 in FIG. 6.

<<Processing Procedure of Personal Authentication Device>>

Figure 7:
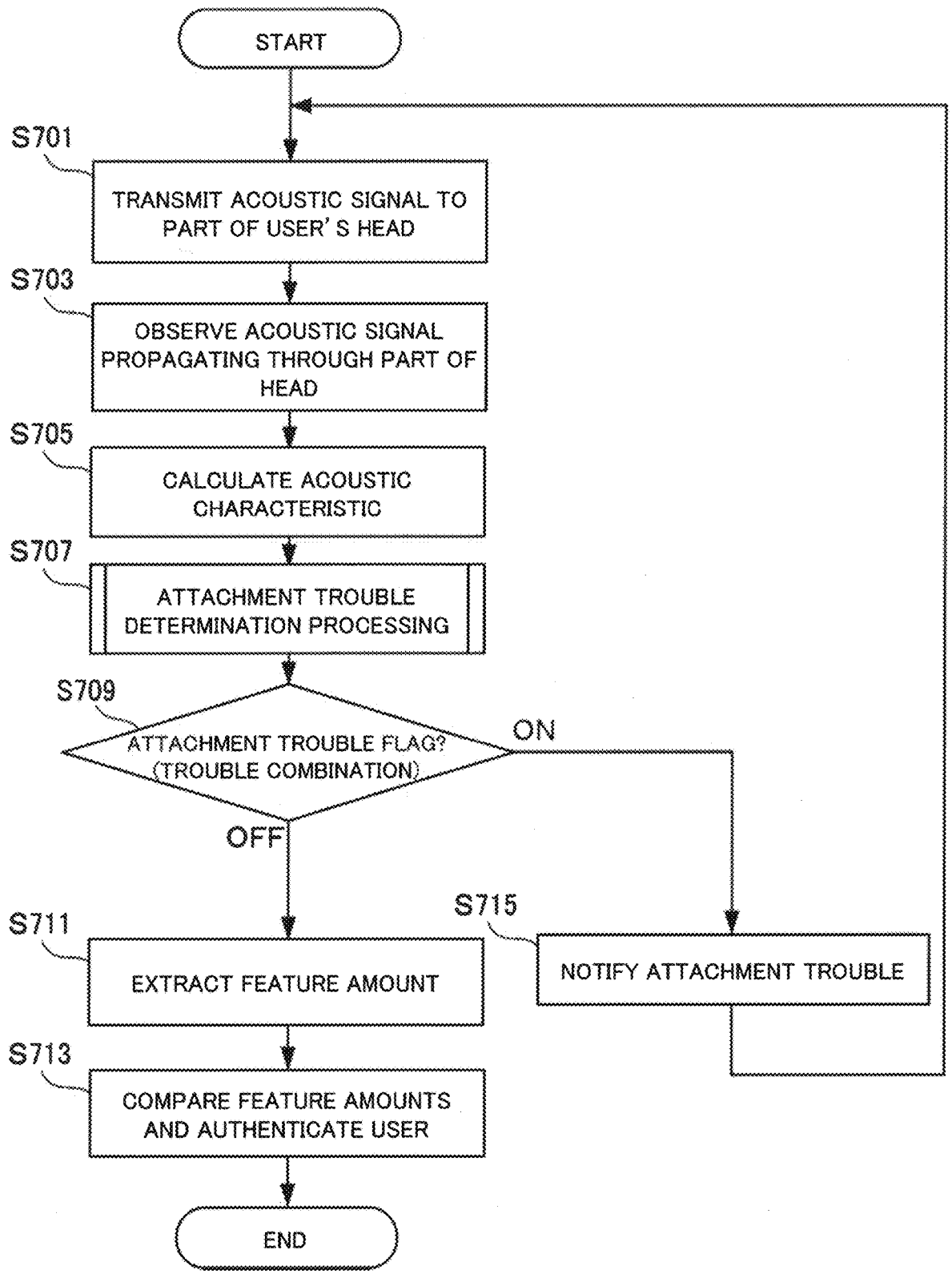
FIG. 7 is a flowchart illustrating a processing procedure of the personal authentication device according to the second example embodiment of the present invention.

FIG. 7 is a flowchart illustrating a processing procedure of personal authentication device 210 according to the present example embodiment. This flowchart is executed by CPU 610 in FIG. 6 using RAM 640, and achieves the functional structural unit in FIG. 3.

In Step S701, personal authentication device 210 transmits an acoustic signal to a part of a head of a user. In Step S703, personal authentication device 210 observes an acoustic signal propagating through the part of the head. In Step S705, personal authentication device 210 calculates an acoustic characteristic from the transmitted acoustic signal and the observed acoustic signal.

In Step S707, personal authentication device 210 executes attachment trouble determination processing by using the calculated acoustic characteristic. In Step S709, personal authentication device 210 determines whether an attachment trouble flag is ON or OFF. When the attachment trouble flag is ON, personal authentication device 210 notifies an attachment trouble in Step S715, the processing returns to Step S701, and personal authentication is repeated. When the attachment trouble flag is OFF, personal authentication device 210 extracts a feature amount from the acoustic characteristic in Step S711. Then, in Step S713, personal authentication device 210 compares the feature amount with a previously stored feature amount and authenticates the user.

(Attachment Trouble Determination Processing)

Figure 8:
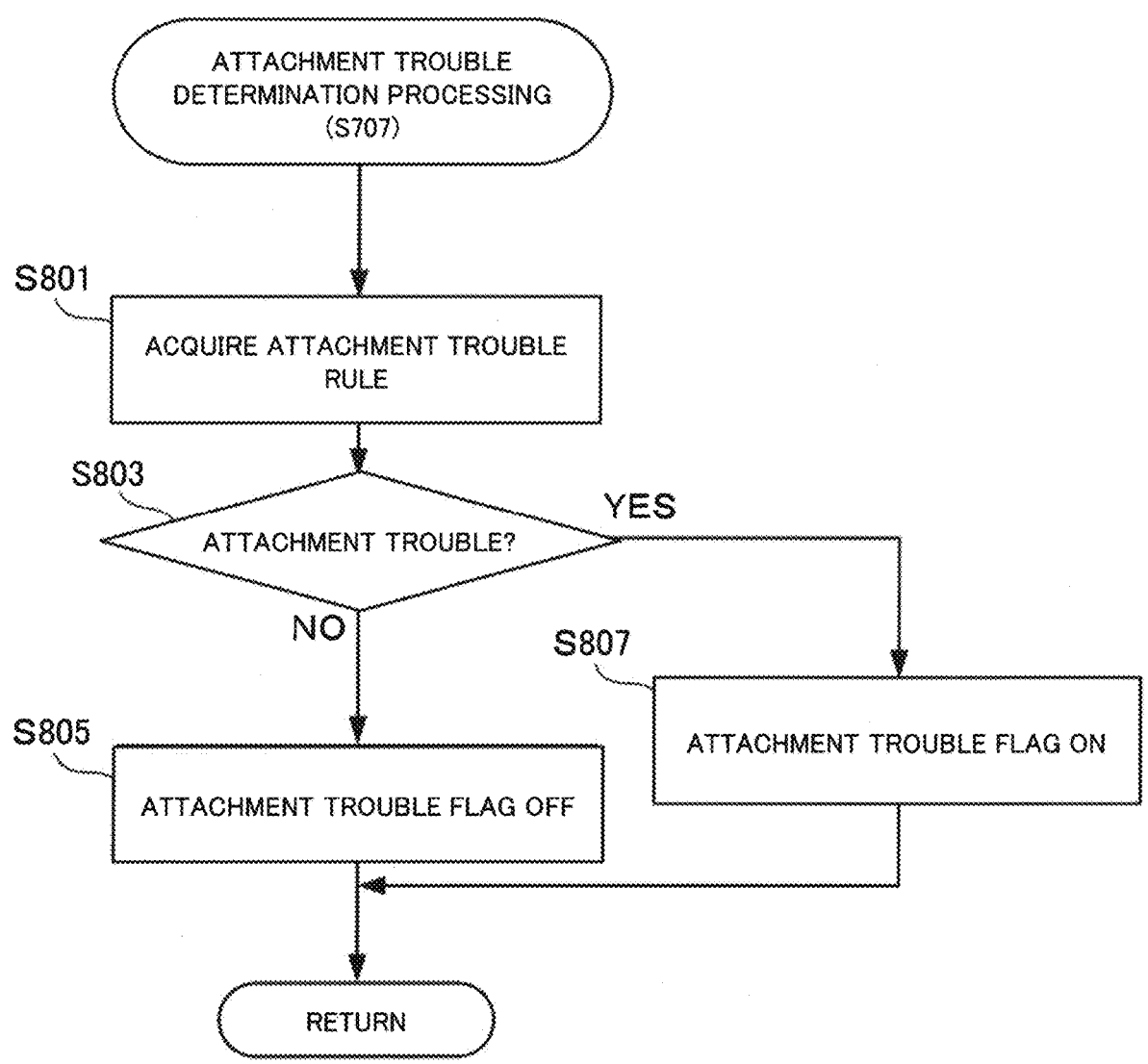
FIG. 8 is a flowchart illustrating a procedure for attachment trouble determination processing according to the second example embodiment of the present invention.

FIG. 8 is a flowchart illustrating a procedure for the attachment trouble determination processing (S707) according to the present example embodiment.

In Step S801, personal authentication device 210 acquires an attachment trouble rule from attachment trouble rule storage unit 302. In Step S803, personal authentication device 210 determines whether or not it is an attachment trouble from a calculated acoustic characteristic according to the attachment trouble rule.

When it is not an attachment trouble, personal authentication device 210 sets an attachment trouble flag to OFF in Step S805, and the processing returns. On the other hand, when it is an attachment trouble, personal authentication device 210 sets the attachment trouble flag to ON in Step S807, and the processing returns.

According to the present example embodiment, when personal authentication device 210 measures an acoustic characteristic of an ear canal of a user by using a headphone or an earphone including a microphone embedded therein, personal authentication device 210 detects whether or not an attachment condition of the headphone or the earphone is suitable for personal authentication. When the attachment condition is not suitable for the personal authentication, personal authentication device 210 prevents a false determination due to the attachment condition of the headphone or the earphone by giving feedback to the user. In this way, a false determination due to an attachment condition of an apparatus that transmits and receives an acoustic signal can be prevented, and accurate personal authentication can be performed.

In other words, a user to be authenticated wears a headphone or an earphone including a microphone embedded therein, and thus an acoustic characteristic of an acoustic signal propagating through a head of the user is measured, and personal authentication is performed. At this time, personal authentication device 210 detects that an attachment state of the attached headphone or earphone is not an appropriate state by comparing the acoustic characteristic with an attachment trouble rule. In this way, personal authentication device 210 can prevent two false determinations caused by an attachment trouble that are false rejection in which the person is mistakenly rejected and false acceptance in which another person is mistakenly accepted. Thus, personal authentication device 210 can achieve the effect of the present example embodiment.

Third Example Embodiment

Next, a personal authentication device according to a third example embodiment of the present invention is described. The personal authentication device according to the present example embodiment is different from that in the second example embodiment described above in that an attachment trouble is detected by using an acoustic characteristic acquired from a specific authentication subject for comparison instead of using a preset reference. In other words, the personal authentication device according to the present example embodiment stores an acoustic characteristic acquired from an acoustic signal previously acquired from a person to be authenticated. The personal authentication device according to the present example embodiment determines that a trouble has occurred in an attachment state of an apparatus when a relationship between a calculated acoustic characteristic and a previously stored acoustic characteristic satisfies an attachment trouble rule. The other configuration and operation are similar to those in the second example embodiment, and thus the same configuration and operation are provided with the same reference signs, and detailed description thereof is omitted.

<<Functional Configuration of Personal Authentication Device>>

Figure 9:
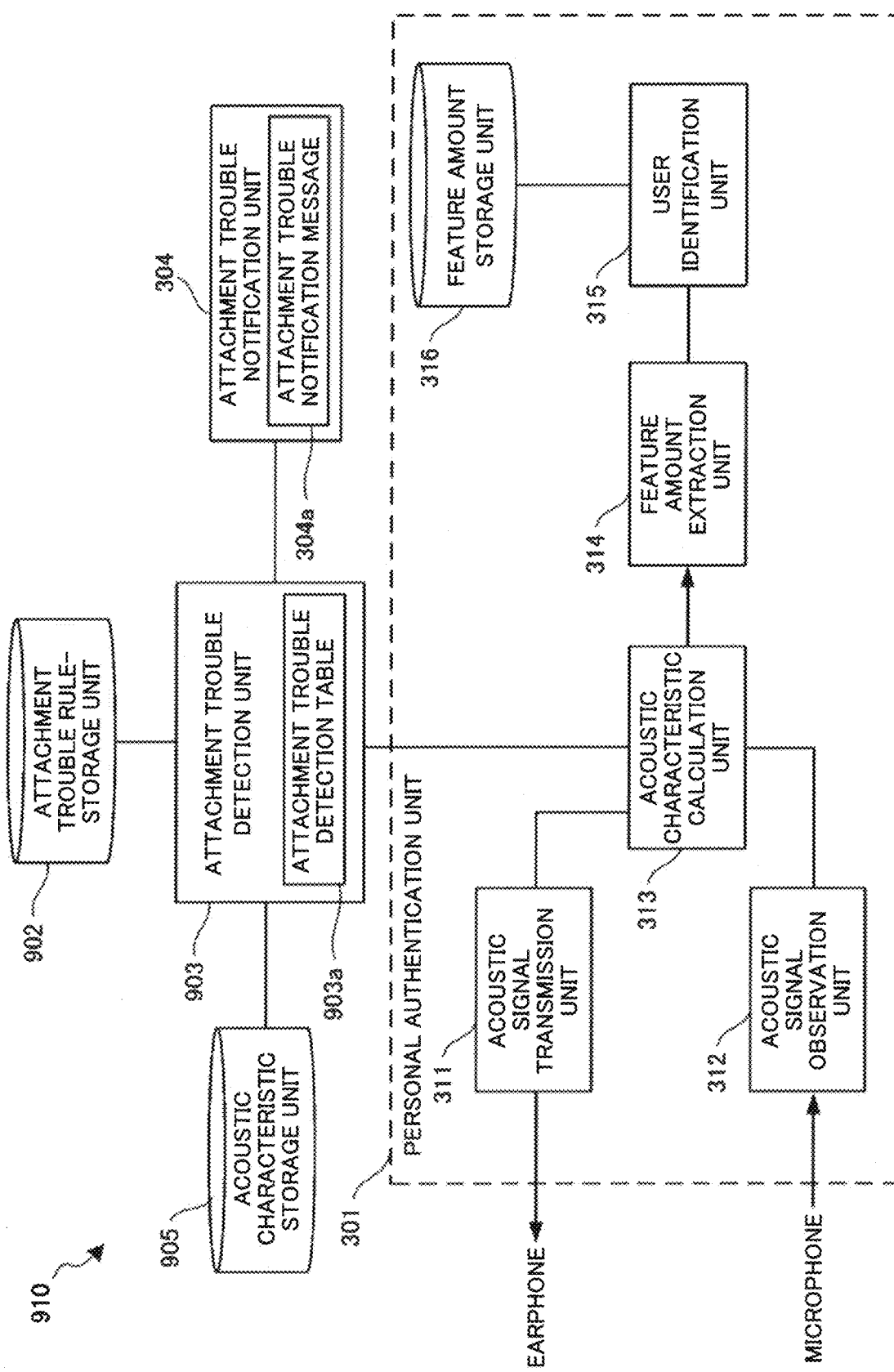
FIG. 9 is a block diagram illustrating a functional configuration of a personal authentication device according to a third example embodiment of the present invention.

FIG. 9 is a block diagram illustrating a functional configuration of personal authentication device 910 according to the present example embodiment. Note that, a functional structural unit in FIG. 9 similar to that in FIG. 3 is provided with same reference sign, and the description thereof is not repeated.

Attachment trouble rule storage unit 902 stores an attachment trouble rule used in the present example embodiment. Acoustic characteristic storage unit 905 stores an acoustic characteristic acquired from an acoustic signal previously acquired from a person to be authenticated. Attachment trouble detection unit 903 includes attachment trouble detection table 903a, and detects an attachment trouble from an acoustic characteristic calculated by acoustic characteristic calculation unit 313 and an acoustic characteristic stored in acoustic characteristic storage unit 905 according to an attachment trouble rule.

(Attachment Trouble Rule-Storage Unit)

FIG. 10A is a diagram illustrating a configuration of attachment trouble rule storage unit 902 according to the present example embodiment. Attachment trouble rule storage unit 902 stores an attachment trouble rule for detecting an attachment trouble from an acoustic characteristic. Note that, a configuration of attachment trouble rule storage unit 902 is not limited to FIG. 10A.

Attachment trouble rule storage unit 902 stores, in association with rule number 1011 that identifies an attachment trouble rule, subject factor 1012 of acoustic characteristic used for attachment trouble detection, attachment trouble condition 1013 in subject factor 1012 of acoustic characteristic, and combination algorithm 1014 of attachment trouble rules used for attachment trouble detection. Note that, each attachment trouble rule may be used alone.

The following examples of attachment trouble rules in the present example embodiment are conceivable.

(Rule Number 21): A value of a factor equivalent to volume among acoustic characteristics is smaller or greater than a value of a factor equivalent to an acoustic characteristic previously acquired from a person to be authenticated.

(Rule Number 22): A value of a factor equivalent to a low frequency (for example, equal to or less than 1 kHz) among acoustic characteristics is smaller or greater than a value of a factor equivalent to an acoustic characteristic previously acquired from a person to be authenticated.

(Rule Number 23): A value of a factor equivalent to volume at a high frequency (for example, equal to or greater than 1 kHz) among acoustic characteristics is smaller or greater than a value of a factor equivalent to an acoustic characteristic previously acquired from a person to be authenticated.

(Rule Number 24): A factor concerned with volume of natural vibration related to a distance from an earphone (acoustic transmission unit) to an eardrum among acoustic characteristics is smaller or greater than a value of a factor equivalent to an acoustic characteristic previously acquired from a person to be authenticated.

(Rule Number 25): A maximum value and a value (peak) greater than two adjacent values among factors equivalent to volume of an acoustic characteristic are smaller than or greater than a value of a corresponding factor of an acoustic characteristic previously acquired from a person to be authenticated.

(Rule Number 26): A frequency of natural vibration related to a distance from an earphone (acoustic transmission unit) to an eardrum among acoustic characteristics is a constant multiple or half of a frequency of corresponding natural vibration of an acoustic characteristic previously acquired from a person to be authenticated.

(Rule Number 27): A frequency of a factor with a maximum value and a factor with a value (peak) greater than two adjacent values, among factors equivalent to volume of an acoustic characteristic, is a constant multiple or half of a frequency of a corresponding factor of an acoustic characteristic previously acquired from a person to be authenticated.

(Acoustic Characteristic Storage Unit)

FIG. 10B is a diagram illustrating a configuration of acoustic characteristic storage unit 905 according to the present example embodiment. Note that, a configuration of acoustic characteristic storage unit 905 is not limited to FIG. 10B.

Acoustic characteristic storage unit 905 stores, in association with person to be authenticated 1051, one or a plurality of attachment trouble rule numbers 1052 and previously acquired information 1053 about a subject factor of an acoustic characteristic corresponding to attachment trouble rule number 1052.

(Attachment Trouble Detection Table)

FIG. 10C is a diagram illustrating a configuration of attachment trouble detection table 903a according to the present example embodiment. Attachment trouble detection table 903a is used as a temporary memory for detecting an attachment trouble by attachment trouble detection unit 903. Note that, a structural component in FIG. 10C similar to that in FIG. 5B is provided with same reference sign, and the description thereof is not repeated.

Subject factor 1022 of acoustic characteristic is information acquired in association with attachment trouble rule number 1023 from acoustic characteristic storage unit 905. Attachment trouble rule number 1023 represents an attachment trouble rule used for determining an attachment trouble.

(Attachment Trouble Determination Processing)

Figure 11:
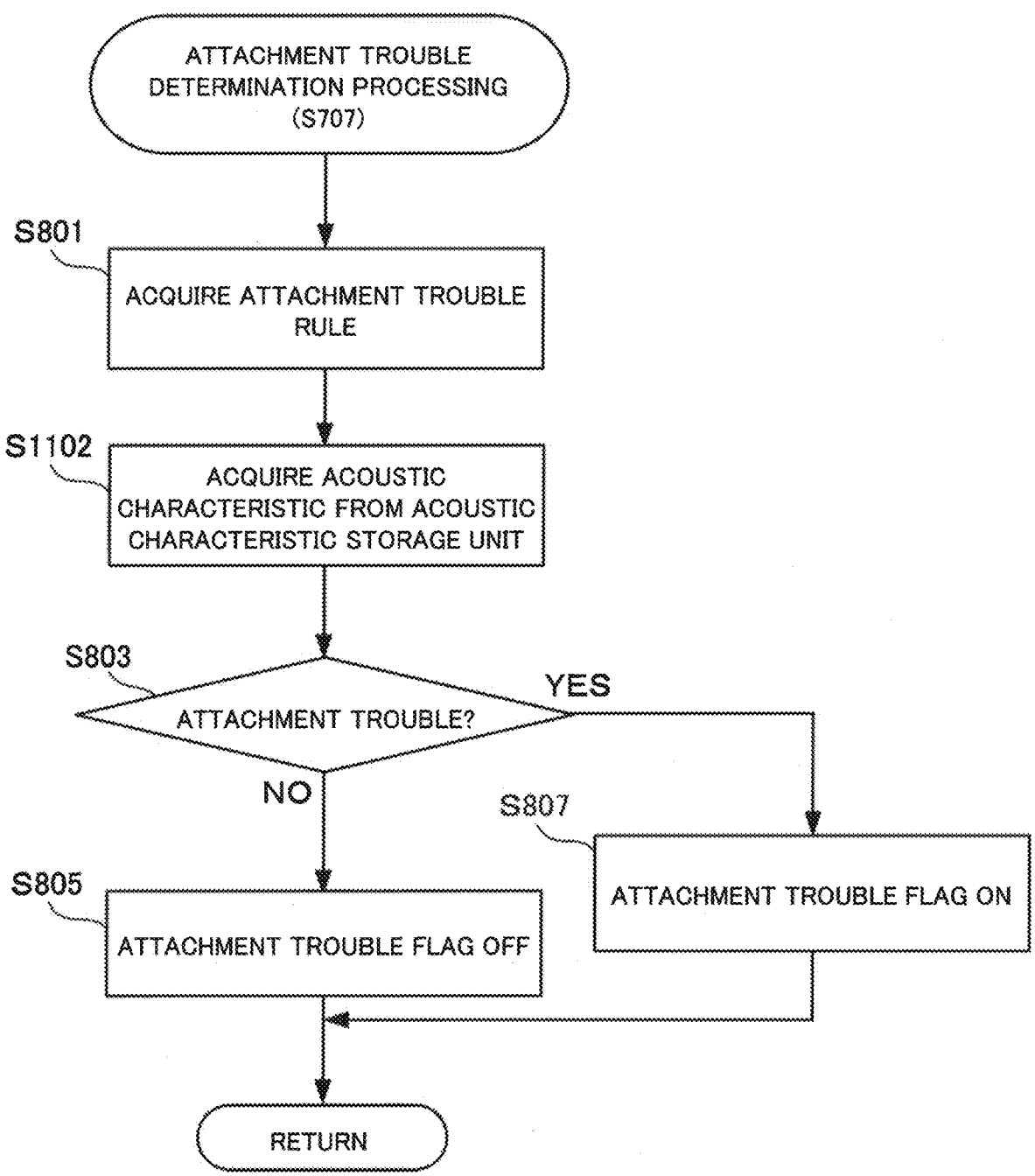
FIG. 11 is a flowchart illustrating a procedure for attachment trouble determination processing according to the third example embodiment of the present invention.

FIG. 11 is a flowchart illustrating a procedure for attachment trouble determination processing (S707) according to the present example embodiment. Note that, the processing procedure in personal authentication device 910 is similar to that in FIG. 7, and FIG. 11 may replace Step S707 in FIG. 7. Further, a step in FIG. 11 similar to that in FIG. 8 is provided with same step number, and the description thereof is not repeated.

In Step S1102, personal authentication device 910 acquires an acoustic characteristic related to an attachment trouble rule from acoustic characteristic storage unit 905.

According to the present example embodiment, by setting a different attachment trouble rule for each person to be authenticated, a false determination due to an attachment condition of an apparatus that transmits and receives an acoustic signal can be prevented, and accurate personal authentication can be performed.

Fourth Example Embodiment

Next, a personal authentication device according to a fourth example embodiment of the present invention is described. The personal authentication device according to the present example embodiment is different from that in the second example embodiment and the third example embodiment described above in that an attachment trouble is detected, based on a feature amount extracted from an acoustic characteristic. Note that, the personal authentication device may use a feature amount extracted in the present example embodiment and an acoustic characteristic in the second example embodiment separately or in combination for detecting an attachment trouble. Further, the personal authentication device may be configured to detect an attachment trouble by comparing a feature amount extracted in the present example embodiment with a feature amount stored in a feature amount storage unit of a personal authentication unit. The other configuration and operation are similar to those in the second example embodiment, and thus the same configuration and operation are provided with the same reference signs, and detailed description thereof is omitted.

<<Functional Configuration of Personal Authentication Device>>

Figure 12:
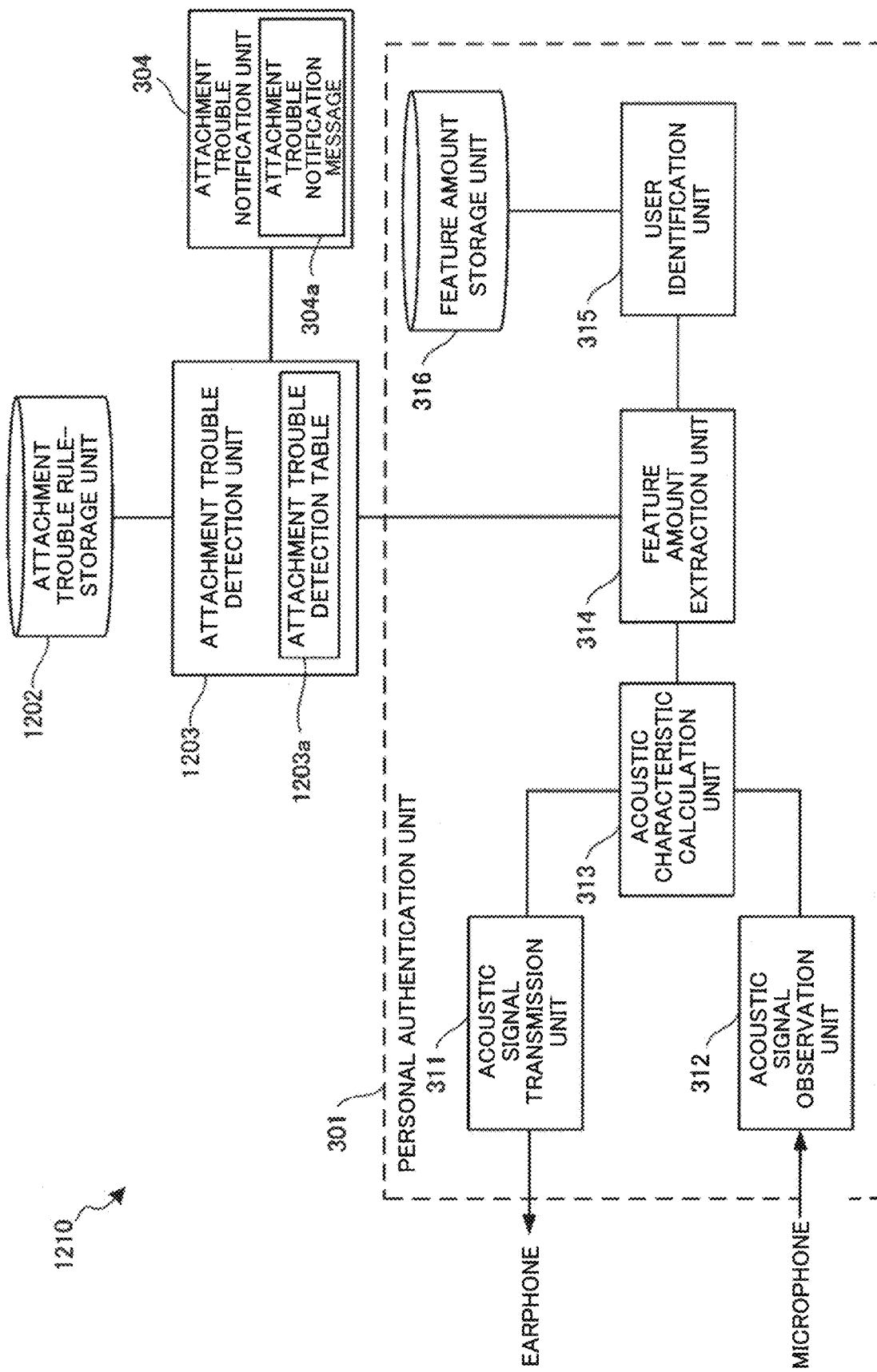
FIG. 12 is a block diagram illustrating a functional configuration of a personal authentication device according to a fourth example embodiment of the present invention.

FIG. 12 is a block diagram illustrating a functional configuration of personal authentication device 1210 according to the present example embodiment. Note that, a functional structural unit in FIG. 12 similar to that in FIG. 3 is provided with same reference sign, and the description thereof is not repeated.

Attachment trouble rule storage unit 1202 stores an attachment trouble rule used in the present example embodiment. Attachment trouble detection unit 1203 includes attachment trouble detection table 1203a, and detects an attachment trouble when a feature amount extracted by feature amount extraction unit 314 satisfies a condition stored in attachment trouble rule storage unit 1202.

(Feature Amount)

As a feature amount, for example, a logarithm spectrum, mel-frequency cepstrum coefficients (MFCC), linear predictive coding coefficients may be used in the present example embodiment. Further, a feature amount acquired by dimensionally compressing a logarithm spectrum, mel-frequency cepstrum coefficients, and linear predictive coding coefficients by using a principal component analysis or a linear discriminative analysis may be used. Further, a feature amount other than this may be used.

Figure 13:
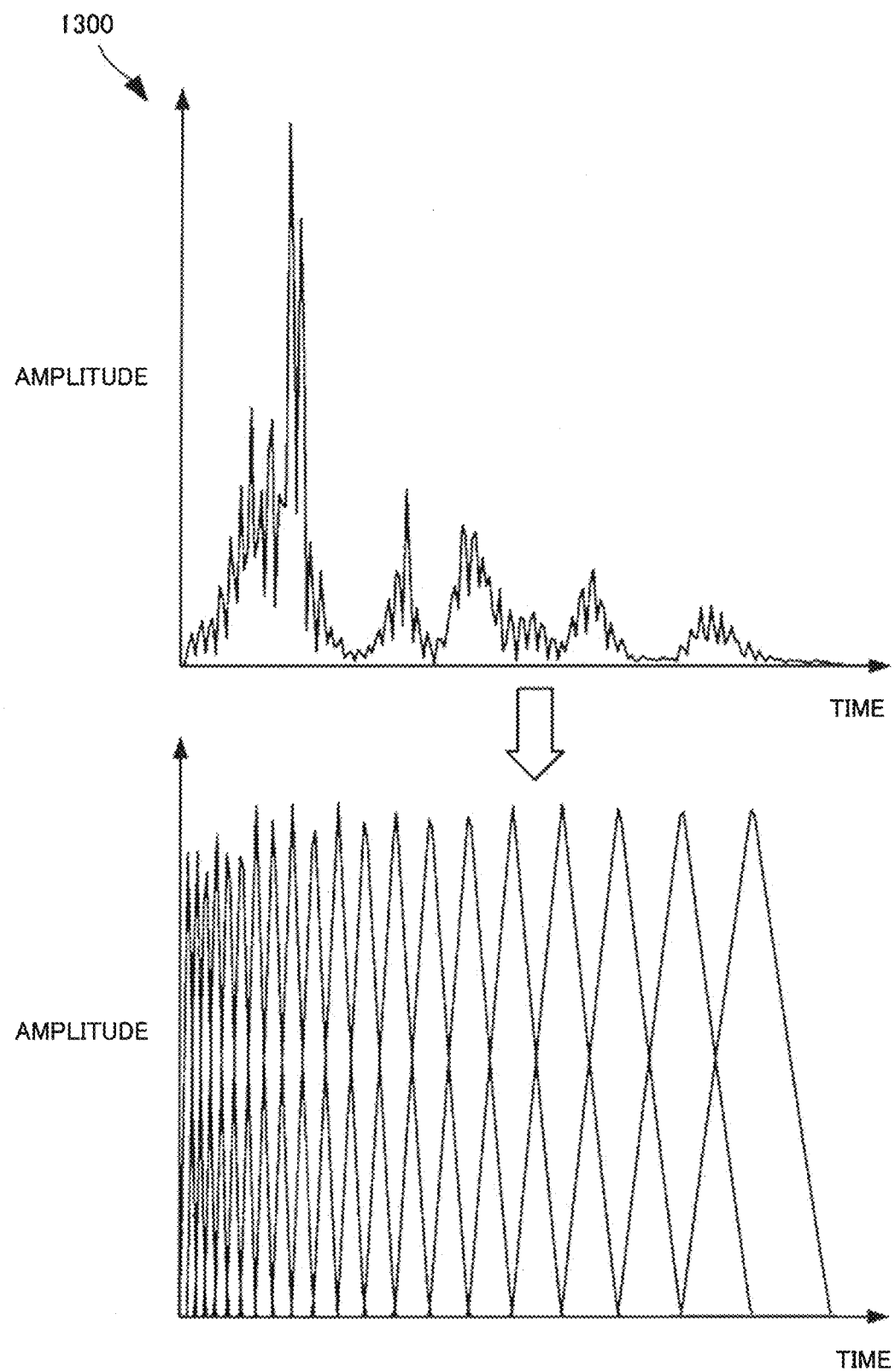
FIG. 13 is a diagram illustrating a feature amount used for personal authentication according to the fourth example embodiment of the present invention.

FIG. 13 is a diagram illustrating related waveform 1300 of MFCC as a feature amount used for personal authentication according to the present example embodiment.

(Attachment Trouble Rule-Storage Unit)

FIG. 14A is a diagram illustrating a configuration of attachment trouble rule storage unit 1202 according to the present example embodiment. Attachment trouble rule storage unit 1202 stores an attachment trouble rule for detecting an attachment trouble from an acoustic characteristic. Note that, a configuration of attachment trouble rule storage unit 1202 is not limited to FIG. 14A.

Attachment trouble rule storage unit 1202 stores, in association with rule number 1411 that identifies an attachment trouble rule, subject factor 1412 of feature amount used for attachment trouble detection, attachment trouble condition 1413 in subject factor 1412 of feature amount, and combination algorithm 1414 of attachment trouble rules used for attachment trouble detection. Note that, each attachment trouble rule may be used alone.

Note that, a rule similar to that in the second example embodiment or the third example embodiment may be used as an attachment trouble rule. Further, when a factor constituting a feature amount is not directly related to volume or volume at a specific frequency, the feature amount may be restored to an acoustic characteristic by being subjected to an arithmetic computation, which is the inverse of calculation that calculates the feature amount, and the acoustic characteristic may be used.

(Attachment Trouble Detection Table)

FIG. 14B is a diagram illustrating a configuration of an attachment trouble detection table according to the present example embodiment. Attachment trouble detection table 1203a is used as a temporary memory for detecting an attachment trouble by attachment trouble detection unit 1203. Note that, a structural component in FIG. 14B similar to that in FIG. 5B is provided with same reference sign, and the description thereof is not repeated.

Subject factor 1421 of attachment trouble detection represents a subject factor of a feature amount used in attachment trouble detection. Subject factor 1422 of feature amount is information acquired from feature amount extraction unit 314. Attachment trouble rule number 1423 represents an attachment trouble rule in the present example embodiment used for determining an attachment trouble.

<<Processing Procedure of Personal Authentication Device>>

Figure 15:
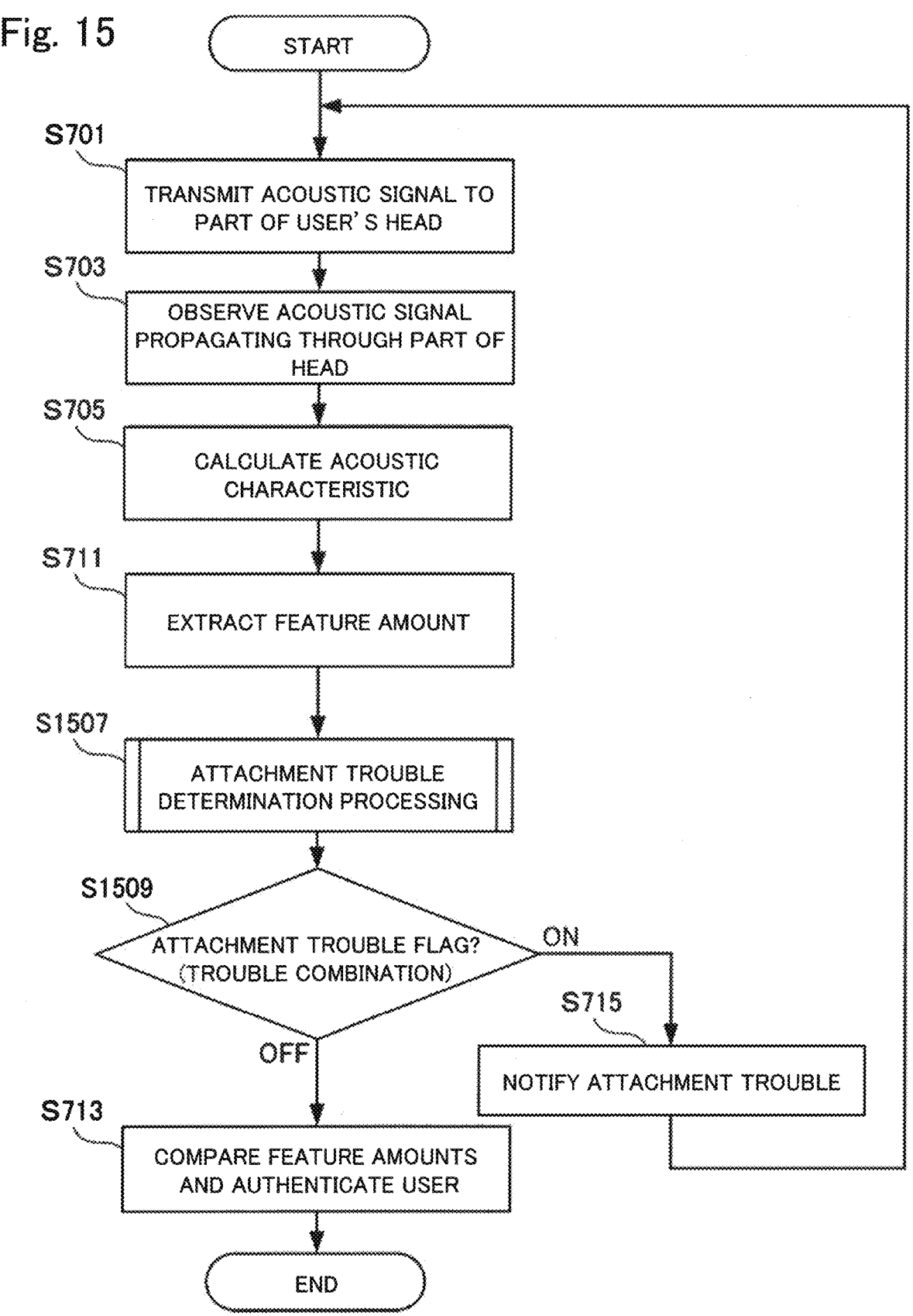
FIG. 15 is a flowchart illustrating a processing procedure of the personal authentication device according to the fourth example embodiment of the present invention.

FIG. 15 is a flowchart illustrating a processing procedure of personal authentication device 1210 according to the present example embodiment. Note that, a step in FIG. 15 similar to that in FIG. 7 is provided with same step number, and the description thereof is not repeated.

In Step S1507, personal authentication device 1210 executes attachment trouble determination processing, based on an attachment trouble rule. Then, in Step S1509, personal authentication device 1210 determines whether an attachment trouble flag is ON or OFF.

Note that, the attachment trouble determination processing in Step S1507 is the same processing in Step S707 in which an acoustic characteristic is replaced by a feature amount.

According to the present example embodiment, by using a feature amount extracted from an acoustic characteristic, a false determination due to an attachment condition of an apparatus that transmits and receives an acoustic signal can be prevented, and accurate personal authentication can be performed.

In other words, a user to be authenticated wears a headphone or an earphone including a microphone embedded therein, and thus an acoustic characteristic of an acoustic signal propagating through a head of the user is measured, and personal authentication is performed. At this time, personal authentication device 1210 detects that an attachment state of the attached headphone or earphone is not an appropriate state by comparing the feature amount extracted from the acoustic characteristic with an attachment trouble rule. In this way, personal authentication device 1210 can prevent two false determinations caused by an attachment trouble that are false rejection in which the person is mistakenly rejected and false acceptance in which another person is mistakenly accepted.

Thus, personal authentication device 1210 can improve authentication accuracy, improve resistance to noise, and reduce an amount of data by determining an attachment trouble, based on a feature amount.

Fifth Example Embodiment

Next, a personal authentication device according to a fifth example embodiment of the present invention is described. The personal authentication device according to the present example embodiment is different from that in the second example embodiment to the fourth example embodiment described above in that an acoustic characteristic is calculated from an acoustic signal propagating through a bone of a head instead of an acoustic signal of an ear canal, and a feature amount is extracted. While sound generally propagates through mainly air as a medium, sound can also propagate through a bone structure as a medium. Propagation of sound through a bone as a medium is referred to as bone conduction. A propagation characteristic of bone conduction also has individuality, and can thus be used for authentication of an individual. Note that, the present example embodiment may also adopt a configuration of attachment trouble detection using a feature amount as in the fourth example embodiment and a configuration in which an acoustic characteristic and a feature amount of an authentication subject are used for comparison as in the third example embodiment. The other configuration and operation are similar to those in the second example embodiment to the fourth example embodiment, and thus the same configuration and operation are provided with the same reference signs, and detailed description thereof is omitted.

<<Functional Configuration of Personal Authentication Device>>

Figure 16:
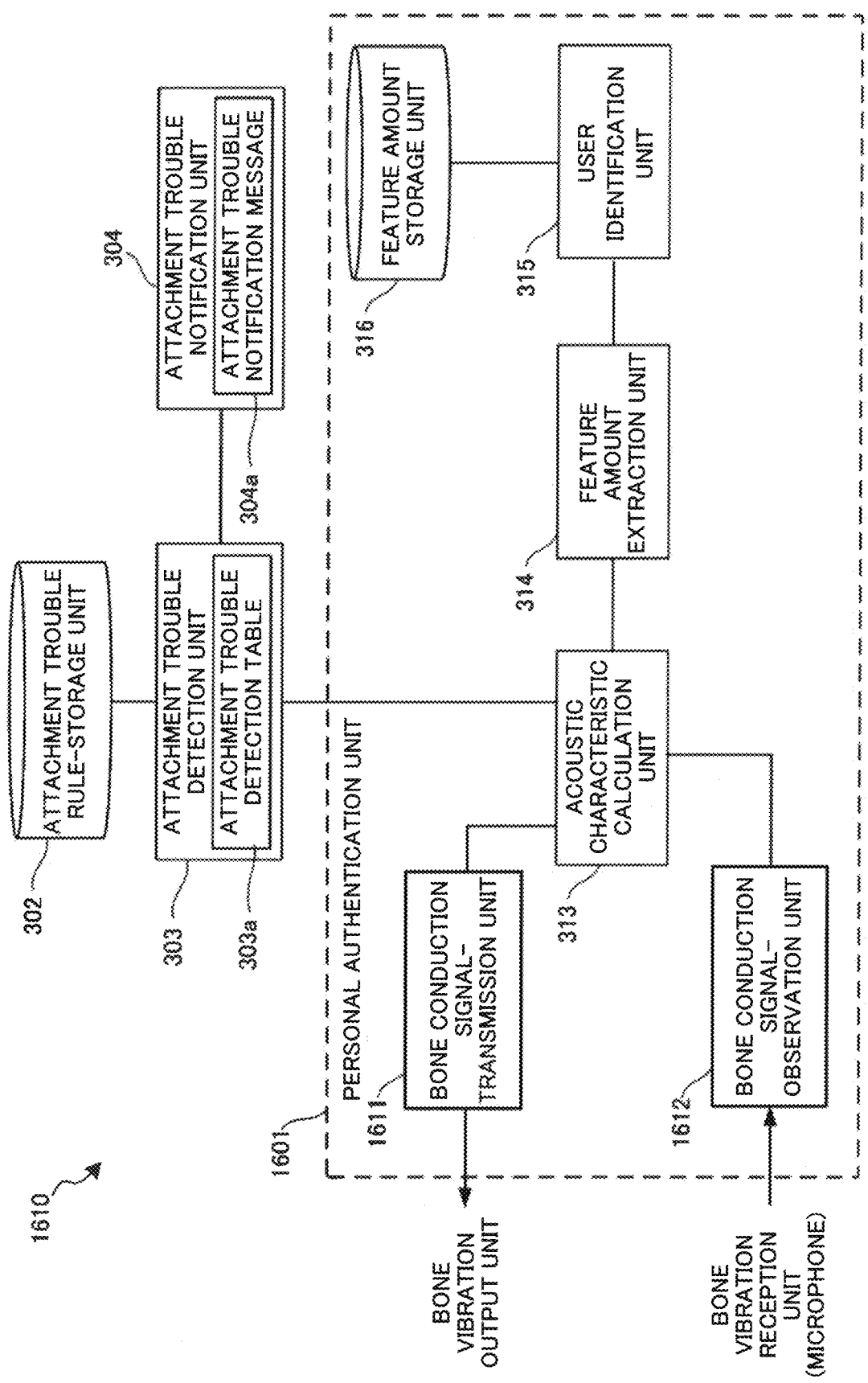
FIG. 16 is a block diagram illustrating a functional configuration of a personal authentication device according to a fifth example embodiment of the present invention.

FIG. 16 is a block diagram illustrating a functional configuration of personal authentication device 1610 according to the present example embodiment. Note that, a functional structural unit in FIG. 16 similar to that in FIG. 3 is provided with same reference sign, and the description thereof is not omitted.

Bone conduction signal-transmission unit 1611 transmits a bone conduction signal being an acoustic signal for bone conduction to a part of a head. Herein, the part of the head to which the bone conduction signal is transmitted is more specifically a region of the head in which a bone is formed, and may be at least a part of a region to which an accessory and an apparatus generating an acoustic effect can be attached or brought close.

Bone conduction signal-observation unit 1612 observes a bone conduction signal (acoustic signal) that has been transmitted from bone conduction signal-transmission unit 1611 and propagated through the part of the head of a user. Herein, the part of the head as a propagation path of the bone conduction signal being the acoustic signal for bone conduction may be more specifically at least a part of a skull constituting a head, a tooth, a brain, a sensory organ, and a cavity between them. Note that, it is assumed that the propagation path includes at least a bone.

Bone conduction signal-observation unit 1612 may be achieved by, for example, a bone conduction microphone. At this time, bone conduction signal-observation unit 1612 may observe an acoustic signal from a part different from an arbitrary part of a head to which bone conduction signal-transmission unit 1611 transmits an acoustic signal.

According to the present example embodiment, by using bone conduction of an acoustic signal in a head, a false determination due to an attachment condition of an apparatus that transmits and receives an acoustic signal can be prevented, and accurate personal authentication can be performed.

Other Example Embodiment

While personal authentication processing and attachment trouble detection processing are performed by a PC in the example embodiments described above, a personal authentication device, a personal authentication method, and a personal authentication program that authenticate an individual by using an audio device can also be provided.

Although the claimed invention has been described with reference to the example embodiments, it should be understood that the claimed invention is not limited to the above-described example embodiments. Various modifications that can be understood by those skilled in the art within the scope of the claimed invention may be applied to the configuration and the details of the claimed invention. Further, a system or a device that combines different features included in the respective example embodiments in any way is also included within the scope of the present invention.

Further, the present invention may be applied to a system including a plurality of apparatuses and may be applied to a single device. Furthermore, the present invention is also applicable to a case where an information processing program realizing functions of the example embodiments is supplied to a system or a device directly or remotely. Therefore, in order to realize functions of the present invention by a computer, a program installed in the computer or a medium that stores the program, and a World Wide Web (WWW) server that causes the program to be downloaded are also included within the scope of the present invention. In particular, a non-transitory computer readable medium that stores a program causing a computer to execute a processing step included in the above-described example embodiments is included within the scope of the present invention.

Other Expression of Example Embodiment

A part or the whole of the above-described example embodiments may also be described in supplementary notes below, which is not limited thereto.

The present invention has been described above by taking the above-described example embodiments as exemplary examples. However, the present invention is not limited to the above-described example embodiments. In other words, various aspects apparent to those skilled in the art may be applied to the present invention within the scope of the present invention.

REFERENCE SIGNS LIST

100 Personal authentication device
101 Personal authentication unit
102 Attachment trouble rule storage unit
200 Personal authentication system
210 Personal authentication device
220 Attached apparatus
230 Sound processor
240 Microphone amplifier
301 Personal authentication unit
302 Attachment trouble rule storage unit
303 Attachment trouble detection unit
304 Attachment trouble notification unit
610 CPU
620 ROM
630 Network interface
640 RAM
650 Storage
660 Input-output interface
661 Display unit
662 Operation unit
663 Voice input-output unit
664 Earphone/microphone control unit
902 Attachment trouble rule storage unit
903 Attachment trouble detection unit
905 Acoustic characteristic storage unit
910 Personal authentication device
1202 Attachment trouble rule storage unit
1203 Attachment trouble detection unit
1210 Personal authentication device
1610 Personal authentication device

The invention claimed is:

1. A personal authentication device worn by a user to be authenticated, the personal authentication device comprising:
a memory storing instructions; and
at least one processor configured to execute the instructions to perform:
determining whether an acoustic characteristic of the user or a feature value extracted from the acoustic characteristic satisfies a predetermined condition in accordance with an attachment trouble rule; and
detecting that there is an attachment trouble of the personal authentication device when the acoustic characteristic or the feature value satisfies a predetermined attachment trouble rule, wherein
the attachment trouble rule includes
(i) sound pressure at natural vibration wavelength corresponding to a distance between an earphone and an eardrum of the user is a constant multiple or half of a predetermined reference, or
(ii) maximum peak value of sound pressure within a frequency band corresponding to the distance between the earphone and the eardrum of the user is a constant multiple or half of a predetermined reference, and the maximum peak value of sound pressure is higher than two adjacent peaks within the frequency band corresponding to the distance from the earphone to the eardrum of the user.

2. The personal authentication device according to claim 1, wherein the acoustic characteristic includes an impulse response, or a transfer function acquired by performing a Fourier transform or a Laplace transform on the impulse response.

3. The personal authentication device according to claim 1, wherein the attachment trouble rule is described on an attachment trouble detection table which associates an attachment trouble rule number and attachment trouble determination flag with an attachment trouble detection subject factor and a feature value subject factor.

4. A personal authentication method for authenticating a user and performed by a computer, the personal authentication method comprising:
determining whether an acoustic characteristic of the user or a feature value extracted from the acoustic characteristic satisfies a predetermined condition in accordance with an attachment trouble rule; and
detecting that there is an attachment trouble of a personal authentication device when the acoustic characteristic or the feature value satisfies a predetermined attachment trouble rule, wherein
the attachment trouble rule includes
(i) sound pressure at natural vibration wavelength corresponding to a distance between an earphone and an eardrum of the user is a constant multiple or half of a predetermined reference, or
(ii) maximum peak value of sound pressure within a frequency band corresponding to the distance between the earphone and the eardrum of the user is a constant multiple or half of a predetermined reference, and the maximum peak value of sound pressure is higher than two adjacent peaks within the frequency band corresponding to the distance from the earphone to the eardrum of the user.

5. The personal authentication method according to claim 4, wherein the acoustic characteristic includes an impulse response, or a transfer function acquired by performing a Fourier transform or a Laplace transform on the impulse response.

6. The personal authentication method according to claim 4, wherein the attachment trouble rule is described on an attachment trouble detection table which associates an attachment trouble rule number and attachment trouble determination flag with an attachment trouble detection subject factor and a feature value subject factor.

7. A non-transitory recording medium storing a person authentication program and executable by a computer to perform processing comprising:
determining whether an acoustic characteristic of a user or a feature value extracted from the acoustic characteristic satisfies a predetermined condition in accordance with an attachment trouble rule; and
detecting that there is an attachment trouble of a personal authentication device when the acoustic characteristic or the feature value satisfies a predetermined attachment trouble rule, wherein
the attachment trouble rule includes
(i) sound pressure at natural vibration wavelength corresponding to a distance between an earphone and an eardrum of the user is a constant multiple or half of a predetermined reference, or (ii) maximum peak value of sound pressure within a frequency band corresponding to the distance between the earphone and the eardrum of the user is a constant multiple or half of a predetermined reference, and the maximum peak value of sound pressure is higher than two adjacent peaks within the frequency band corresponding to the distance from the earphone to the eardrum of the user.

8. The non-transitory recording medium according to claim 7, wherein the acoustic characteristic includes an impulse response, or a transfer function acquired by performing a Fourier transform or a Laplace transform on the impulse response.

9. The non-transitory recording medium according to claim 7, wherein the attachment trouble rule is described on an attachment trouble detection table which associates an attachment trouble rule number and attachment trouble determination flag with an attachment trouble detection subject factor and a feature value subject factor.

* * * * *